(12) United States Patent
Amplatz et al.

(10) Patent No.: US 11,134,933 B2
(45) Date of Patent: Oct. 5, 2021

(54) MULTI-LAYER BRAIDED STRUCTURES FOR OCCLUDING VASCULAR DEFECTS

(71) Applicant: St. Jude Medical, Cardiology Division, Inc., St. Paul, MN (US)

(72) Inventors: Kurt Amplatz, St. Paul, MN (US); Matt Glimsdale, St. Michael, MN (US); Jana Santer, Spring Lake, MN (US); Derek Wise, New Brighton, MN (US); John C. Oslund, Blaine, MN (US); Kent Anderson, Champlin, MN (US); Daniel O. Adams, Long Lake, MN (US); Zhong Qian, Maple Grove, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 298 days.

(21) Appl. No.: 16/246,811

(22) Filed: Jan. 14, 2019

(65) Prior Publication Data

US 2019/0142406 A1 May 16, 2019

Related U.S. Application Data

(63) Continuation of application No. 14/593,625, filed on Jan. 9, 2015, which is a continuation of application (Continued)

(51) Int. Cl.
*A61B 17/00* (2006.01)
*A61B 17/12* (2006.01)

(52) U.S. Cl.
CPC .... *A61B 17/0057* (2013.01); *A61B 17/12031* (2013.01); *A61B 17/12109* (2013.01); (Continued)

(58) Field of Classification Search
CPC .......... A61B 17/0057; A61B 17/12031; A61B 17/12109; A61B 17/12122; A61B 17/12172; A61B 2017/00575; A61B 2017/00606; A61B 2017/00632; A61B 2017/00867
See application file for complete search history.

(56) References Cited

U.S. PATENT DOCUMENTS

| 2,083,257 A | 6/1937 | Dyment |
| 3,834,388 A | 9/1974 | Sauer |

(Continued)

FOREIGN PATENT DOCUMENTS

| CA | 2501033 A1 | 9/2005 |
| CN | 1218379 A | 6/1999 |

(Continued)

*Primary Examiner* — Thomas McEvoy
(74) *Attorney, Agent, or Firm* — Armstrong Teasdale LLP

(57) ABSTRACT

A collapsible medical device and associated methods of occluding an abnormal opening in, for example, a body organ, wherein the medical device is shaped from plural layers of a heat-treatable metal fabric. Each of the fabric layers is formed from a plurality of metal strands and the assembly is heat-treated within a mold in order to substantially set a desired shape of the device. By incorporating plural layers in the thus-formed medical device, the ability of the device to rapidly occlude an abnormal opening in a body organ is significantly improved.

14 Claims, 19 Drawing Sheets

Related U.S. Application Data

No. 14/282,134, filed on May 20, 2014, now Pat. No. 9,445,799, which is a continuation of application No. 11/820,841, filed on Jun. 21, 2007, now Pat. No. 8,777,974, which is a continuation-in-part of application No. 11/473,971, filed on Jun. 23, 2006, now Pat. No. 8,398,670, which is a continuation-in-part of application No. 10/804,993, filed on Mar. 19, 2004, now abandoned.

(52) U.S. Cl.
CPC .. *A61B 17/12122* (2013.01); *A61B 17/12159* (2013.01); *A61B 17/12163* (2013.01); *A61B 17/12172* (2013.01); *A61B 2017/00575* (2013.01); *A61B 2017/00592* (2013.01); *A61B 2017/00606* (2013.01); *A61B 2017/00632* (2013.01); *A61B 2017/00867* (2013.01); *A61B 2017/12127* (2013.01); *A61F 2250/0069* (2013.01)

(56) References Cited

U.S. PATENT DOCUMENTS

| | | | |
|---|---|---|---|
| 3,874,388 A | 4/1975 | King | |
| 4,304,010 A | 12/1981 | Mano | |
| 4,441,215 A | 4/1984 | Kaster | |
| 4,655,771 A | 4/1987 | Wallsten | |
| 4,728,328 A | 3/1988 | Hughes | |
| 4,836,204 A | 6/1989 | Landymore | |
| 4,917,089 A | 4/1990 | Sideris | |
| 4,921,484 A | 5/1990 | Hillstead | |
| 4,991,602 A | 2/1991 | Amplatz | |
| 5,064,435 A | 11/1991 | Porter | |
| 5,067,489 A | 11/1991 | Lind | |
| 5,108,420 A | 4/1992 | Marks | |
| 5,334,217 A | 8/1994 | Das | |
| 5,522,822 A | 6/1996 | Phelps | |
| 5,522,881 A | 6/1996 | Lentz | |
| 5,562,725 A | 10/1996 | Schmitt | |
| 5,628,788 A | 5/1997 | Pinchuk | |
| 5,709,707 A | 1/1998 | Lock | |
| 5,709,713 A | 1/1998 | Evans | |
| 5,724,552 A | 3/1998 | Taoda | |
| 5,725,552 A | 3/1998 | Kotula | |
| 5,741,325 A | 4/1998 | Chaikof | |
| 5,755,772 A | 5/1998 | Evans | |
| 5,758,562 A | 6/1998 | Thompson | |
| 5,800,508 A | 9/1998 | Goicoechea | |
| 5,846,261 A | 12/1998 | Kotula | |
| 5,865,791 A | 2/1999 | Whayne | |
| 5,906,641 A | 5/1999 | Thompson | |
| 5,916,264 A | 6/1999 | Von Oepen | |
| 5,928,260 A | 7/1999 | Chin | |
| 5,944,738 A | 8/1999 | Amplatz | |
| 5,957,974 A | 9/1999 | Thompson | |
| 5,984,917 A | 11/1999 | Fleischman | |
| 5,994,738 A | 11/1999 | Wollesen | |
| 6,042,592 A | 3/2000 | Schmitt | |
| 6,059,812 A | 5/2000 | Clerc | |
| 6,066,776 A | 5/2000 | Goodwin | |
| 6,083,257 A | 7/2000 | Taylor | |
| 6,096,052 A | 8/2000 | Callister | |
| 6,110,198 A | 8/2000 | Fogarty | |
| 6,123,715 A | 9/2000 | Amplatz | |
| 6,132,438 A | 10/2000 | Fleischman | |
| 6,152,144 A | 11/2000 | Lesh | |
| 6,156,064 A | 12/2000 | Chouinard | |
| 6,168,615 B1 | 1/2001 | Ken | |
| 6,168,622 B1* | 1/2001 | Mazzocchi | A61B 17/0057 606/200 |
| 6,187,025 B1 | 2/2001 | Machek | |
| 6,214,029 B1 | 4/2001 | Thill | |
| 6,241,768 B1 | 6/2001 | Agarwal | |
| 6,267,775 B1 | 7/2001 | Clerc | |
| 6,299,636 B1 | 10/2001 | Schmitt | |
| 6,346,117 B1 | 2/2002 | Greenhalgh | |
| 6,368,339 B1* | 4/2002 | Amplatz | B21F 45/008 606/200 |
| 6,379,366 B1 | 4/2002 | Fleischman | |
| 6,428,558 B1 | 8/2002 | Jones | |
| 6,447,531 B1 | 9/2002 | Amplatz | |
| 6,468,301 B1 | 10/2002 | Amplatz | |
| 6,468,303 B1 | 10/2002 | Amplatz | |
| 6,469,303 B1 | 10/2002 | Sun | |
| 6,475,227 B2 | 11/2002 | Burke | |
| 6,488,705 B2 | 12/2002 | Schmitt | |
| 6,494,907 B1 | 12/2002 | Bulver | |
| 6,500,203 B1 | 12/2002 | Thompson | |
| 6,551,303 B1 | 4/2003 | Van Tassel | |
| 6,599,308 B2 | 7/2003 | Amplatz | |
| 6,652,555 B1 | 11/2003 | Vantassel | |
| 6,652,556 B1 | 11/2003 | Vantassel | |
| 6,682,546 B2 | 1/2004 | Amplatz | |
| 6,709,451 B1 | 3/2004 | Noble | |
| 6,709,455 B1 | 3/2004 | Chouinard | |
| 6,730,108 B2 | 5/2004 | Van Tassel | |
| 6,773,448 B2 | 8/2004 | Kusleika | |
| 6,830,576 B2 | 12/2004 | Fleischman | |
| 6,860,900 B2 | 3/2005 | Clerc | |
| 6,866,679 B2 | 3/2005 | Kusleika | |
| 6,911,037 B2 | 6/2005 | Gainor | |
| 6,932,837 B2 | 8/2005 | Amplatz | |
| 6,949,113 B2 | 9/2005 | Van Tassel | |
| 6,974,586 B2 | 12/2005 | Greenhalgh | |
| 7,025,779 B2 | 4/2006 | Elliott | |
| 7,029,494 B2 | 4/2006 | Soun | |
| 7,044,134 B2 | 5/2006 | Khairkhahan | |
| 7,052,513 B2 | 5/2006 | Thompson | |
| 7,128,073 B1 | 10/2006 | Van Der Burg | |
| 7,147,656 B2 | 12/2006 | Andreas | |
| 7,152,605 B2 | 12/2006 | Khairkhahan | |
| 7,169,164 B2 | 1/2007 | Borillo | |
| 7,678,123 B2 | 3/2010 | Chanduszko | |
| 8,621,975 B2 | 1/2014 | Russo | |
| 2002/0068950 A1 | 6/2002 | Corcoran | |
| 2002/0099437 A1 | 7/2002 | Anson | |
| 2002/0143349 A1 | 10/2002 | Gifford | |
| 2002/0169473 A1* | 11/2002 | Sepetka | A61L 31/145 606/200 |
| 2003/0135265 A1 | 7/2003 | Stinson | |
| 2003/0135268 A1 | 7/2003 | Desai | |
| 2003/0195553 A1 | 10/2003 | Wallace | |
| 2004/0143293 A1 | 7/2004 | Marino | |
| 2005/0209633 A1* | 9/2005 | Callister | A61B 17/12104 606/200 |
| 2005/0209636 A1 | 9/2005 | Widomski | |
| 2005/0267510 A1 | 12/2005 | Razack | |
| 2006/0004404 A1 | 1/2006 | Khachin | |
| 2006/0135947 A1 | 6/2006 | Soltesz | |
| 2006/0224183 A1 | 10/2006 | Freudenthal | |
| 2007/0112380 A1 | 5/2007 | Figulla | |
| 2007/0112381 A1 | 5/2007 | Figulla | |
| 2007/0168018 A1 | 7/2007 | Amplatz | |
| 2007/0168019 A1 | 7/2007 | Amplatz | |
| 2007/0225760 A1 | 9/2007 | Moszner | |
| 2007/0265656 A1 | 11/2007 | Amplatz | |
| 2007/0265658 A1 | 11/2007 | Nelson | |
| 2008/0200945 A1 | 8/2008 | Amplatz | |
| 2009/0062841 A1 | 3/2009 | Amplatz | |
| 2009/0210048 A1 | 8/2009 | Amplatz | |
| 2010/0000797 A1 | 1/2010 | Kataja | |
| 2011/0184508 A2 | 7/2011 | Burmeister | |
| 2013/0012979 A1 | 1/2013 | Amplatz | |

FOREIGN PATENT DOCUMENTS

| | | | |
|---|---|---|---|
| CN | 1269707 A | 10/2000 | |
| CN | 1672644 A | 9/2005 | |
| CN | 1736346 A | 2/2006 | |
| DE | 10338702 B3 | 3/2005 | |
| DE | 10338702 B9 | 4/2007 | |
| EP | 1576929 A2 | 9/2005 | |

(56) References Cited

FOREIGN PATENT DOCUMENTS

| | | | |
|---|---:|---|---|
| EP | 1923019 | A1 | 5/2008 |
| JP | 2001515748 | A | 9/2001 |
| JP | 2002119515 | A | 4/2002 |
| JP | 2005261951 | A | 9/2005 |
| JP | 2005528181 | A | 9/2005 |
| WO | 9601599 | A1 | 1/1996 |
| WO | 9731672 | A1 | 9/1997 |
| WO | 9742878 | A1 | 11/1997 |
| WO | 9847430 | A1 | 10/1998 |
| WO | 9912478 | A1 | 3/1999 |
| WO | 9939646 | A1 | 8/1999 |
| WO | 0013624 | A2 | 3/2000 |
| WO | 0028923 | A1 | 5/2000 |
| WO | 0172367 | A1 | 10/2001 |
| WO | 2004064671 | A2 | 8/2004 |
| WO | 2005074845 | A1 | 8/2005 |

\* cited by examiner

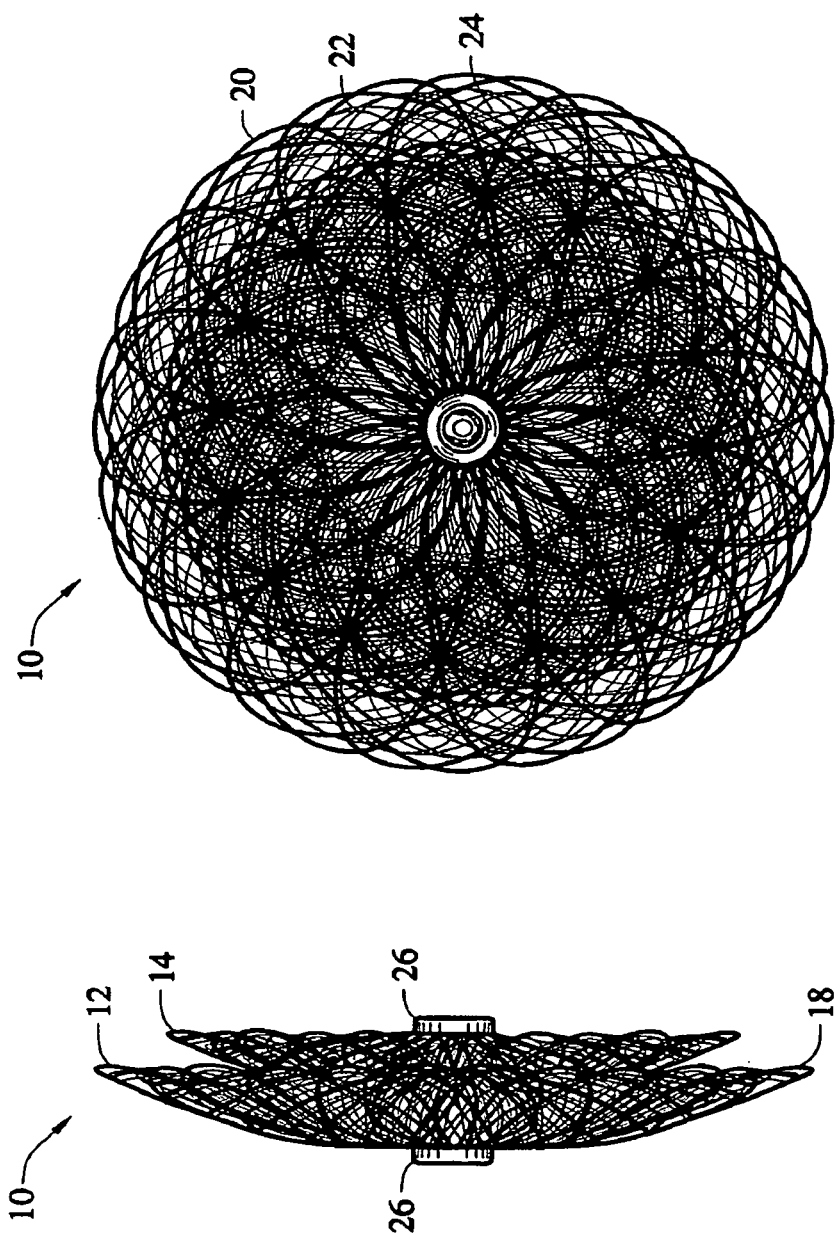

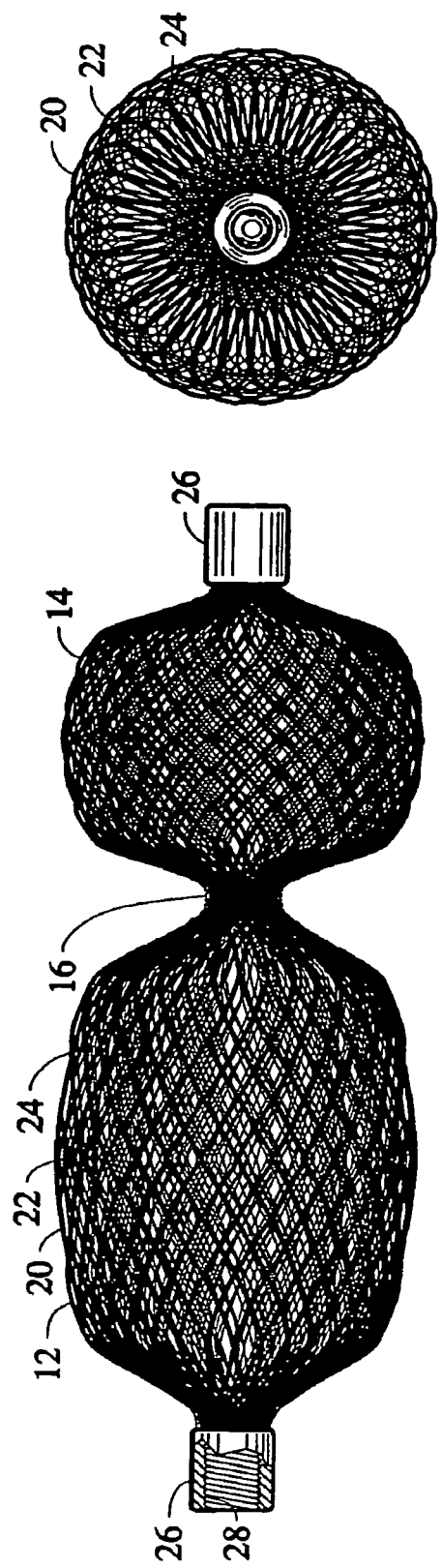

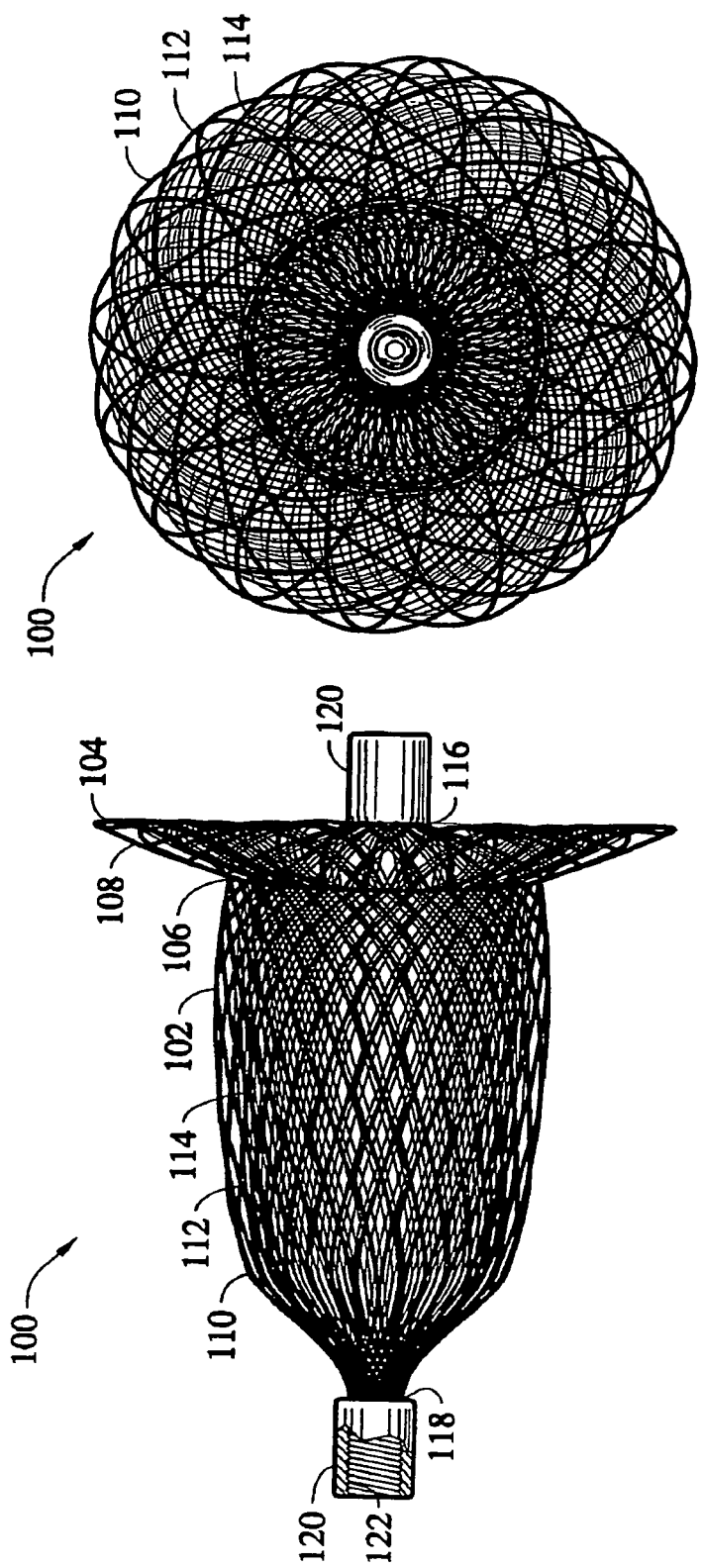

MULTI-LAYER BRAIDED STRUCTURES FOR OCCLUDING VASCULAR DEFECTS

CROSS-REFERENCE TO RELATED APPLICATIONS

This application is a continuation of U.S. continuation application Ser. No. 14/593,625, filed on Jan. 9, 2015, which is a continuation of U.S. continuation application Ser. No. 14/282,134, filed on May 20, 2014, which is a continuation of U.S. continuation-in-part application Ser. No. 11/820,841, filed on Jun. 21, 2007, which is a continuation-in-part of application Ser. No. 11/473,971, filed Jun. 23, 2006, which is a continuation-in-part of application Ser. No. 10/804,993, filed Mar. 19, 2004, all above applications of which are incorporated herein by reference in their entireties.

BACKGROUND OF THE INVENTION

Field of the Invention

The present invention generally relates to intravascular devices for treating certain medical conditions and, more particularly, relates to a low profile intravascular occlusion devices for treating congenital defects including Atrial and Ventricular Septal Defects (ASD and VSD respectively), Patent Ductus Arteriosus (PDA) and Patent Foramen Ovale (PFO) as well as conditions that result from previous medical procedures such as Para-Valvular Leaks (PVL) following surgical valve repair or replacement. The devices made in accordance with the invention are particularly well suited for delivery through a catheter or the like to a remote location in a patient's heart or in analogous vessels or organs within a patient's body.

Description of the Related Art

A wide variety of intra cardiac prosthetic devices are used in various medical procedures. For example, certain intravascular devices, such as catheters and guide wires, are generally used simply to deliver fluids or other medical devices to specific locations within the vascular system of a patient, such as a selective coronary artery. Other, frequently more complex, devices are used in treating specific conditions, such as devices used in removing vascular occlusions or for treating septal defects and the like.

In certain circumstances, it may be necessary to occlude a patient's vessel, such as to stop blood flow through an artery to a tumor or other lesion. Presently, this is commonly accomplished simply by inserting, for example, Ivalon particles (a trade name for vascular occlusion particles) and short sections of coil springs into a vessel at a desired location. These "embolization agents" will eventually become lodged in the vessel, frequently floating downstream of the site at which they are released before blocking the vessel. This procedure is often limited in its utility, in part, due to the inability to precisely position the embolization agents. These embolization agents are not commonly used as an intra cardiac occluding device.

Physicians may temporarily occlude a septal defect until the patient stabilizes enough for open-heart surgical procedures and have used balloon catheters similar to that disclosed by Landymore et al. in U.S. Pat. No. 4,836,204. When using such a catheter, an expandable balloon is carried on a distal end of a catheter. When the catheter is guided to the desired location, the balloon is inflated with a fluid until it substantially fills the defect and becomes lodged therein. Resins, which will harden inside the balloon, such as an acrylonitrile, can be employed to permanently fix the size and shape of the balloon. The balloon can then be detached from the end of the catheter and left in place. If the balloon is not filled enough, it will not be firmly lodged in the septal defect and may rotate and loosen from the septal wall, thereby being released into the blood flowing from the right or left ventricular chamber. Overfilling the balloon is an equally undesirable occurrence, which may lead to the rupture of the balloon and release of resins into the patient's bloodstream.

Mechanical embolization devices, filters and traps have been proposed in the past, representative examples of which are disclosed in King et al., U.S. Pat. No. 3,874,388 (the '388 patent), Das, U.S. Pat. No. 5,334,217 (the '217 patent), Sideris, U.S. Pat. No. 4,917,089 (the '089 patent) and Marks, U.S. Pat. No. 5,108,420 (the '420 patent). The '388, '217, '089, and '420 devices are typically pre-loaded into an introducer or delivery catheter and are not commonly loaded by the physician during the medical procedure. During deployment of these devices, recapture into the delivery catheter is difficult if not impossible, thereby limiting the effectiveness of these devices.

Significantly, the size of these devices is inherently limited by the structure and form of the device. When using occluding devices, such as in the above-identified '089, '388, '217, or '420 patent (plugs to occlude septal defects), the pressure and therefore the chance of dislodgment of the device increases with the size of the defect. Consequently, these devices must have a very large retention skirt positioned on each side of the defect. Oftentimes, the position of the septal defect dictates the size of the retention skirt. In a membranous type septal defect, it is difficult, if not impossible to be able to effectively position the '388, '217, '089, or '420 device without at least partially closing off the aorta. Also, these disclosed devices tend to be rather expensive and time-consuming to manufacture. Hence, it is desirable to provide a low profile device that is recoverable and retractable into the delivery system without increasing the overall thickness of the device. The desired device should also be made with a relatively small retention skirt so as to be positionable within a membranous type septal defect without closing off the aorta.

It the case of a membranous ventricular septal defect, if the central diameter of the occluder is exerting too much pressure on the septum, heart block may occur, and if the retention skirt is too large, it may interfere with the opening and closing of the aortic valve. The stiffness required to retain the current devices in place against blood pressure makes them more difficult to deliver. Hence, there is a need for a low profile, easy to deliver device, that can be shaped for retention without blocking off the aorta or aortic valve and which is conformable without exerting excess pressure on tissue near conductive pathways.

It the case of PDA's, a smaller, lower profile device that can fit through a 4 French catheter potentially allows treatment of pre-mature infants with a PDA. These patients are current sent to surgery because the use of coils to occlude the PDA, are not suitable due to the size of the PDA anatomy.

Also, the shape of the prior art devices (for example, squares, triangles, pentagons, hexagons and octagons) requires a larger contact area, having corners, which extend to the free wall of the atria. Each time the atria contracts (approximately 100,000 times per day), internal wires within the prior art devices, such as described in the Das '217 patent, are flexed, creating structural fatigue fractures in approximately 30 percent of all cases. The sharp corners of these devices resulted in a high percentage of cardiac perforations and they were, therefore, withdrawn from the market. Furthermore, the previous devices require a 14-16 French introducing catheter, making it impossible to treat children affected with congenital defects with these devices.

Accordingly, it would be advantageous to provide a reliable occlusion device which is both easy to deploy through a 4-7 French catheter and which can be accurately placed in a vessel or organ. It would also be desirable to provide a low-profile recoverable device for deployment in an organ of a patient's body.

In the Kotula et al. U.S. Pat. No. 5,846,261, there is described a reliable, low-profile, intra cardiac occlusion device which may be formed to treat, for example, Ventricular Septal Defects (VSD), Atrial Septal Defects (hereinafter ASD), and Patent Ductus Arteriosus (hereinafter PDA). When forming these intravascular devices from a resilient metal fabric, a plurality of resilient strands exhibiting a memory property are provided, with the wires being formed by braiding to create a resilient material. This braided fabric is then deformed to generally conform to a molding surface of a molding element and the braided fabric is heat treated in contact with the surface of the molding element at an elevated temperature. The time and temperature of the heat treatment is selected to substantially set the braided fabric in its deformed state. After the heat treatment, the fabric is removed from contact with the molding element and it will substantially retain its shape in the deformed state. The braided fabric so treated defines an expanded state of a medical device, which can be deployed through a catheter into a channel in a patient's body.

Embodiments of the Kotula et al. invention provide specific shapes for medical devices, which may be made in accordance with that invention to address identified medical needs and procedures. The devices have an expanded low-profile configuration and may include recessed clamps that gather and hold the ends of the braided metal fabric to prevent unraveling and that attach to an end of a delivery device or guide wire, allowing recovery of the device after placement. In use, a guide catheter is positioned and advanced in a patient's body such that the distal end of the catheter is adjacent a desired treatment site for treating a physiological condition. A preselected medical device, made in accordance with the Kotula et al. invention and having a predetermined shape, is then collapsed by longitudinally stretching and is inserted into the lumen of the catheter. The device is urged through the catheter and out the distal end whereupon, due to its memory property, it will tend to substantially return to its expanded, relaxed state adjacent the treatment site. The guide wire or delivery catheter is then released from the clamp and removed.

In accordance with a first of these embodiments, a generally elongate medical device has a generally tubular middle portion and a pair of expanded diameter portions, with one expanded diameter portion positioned at either end of the middle portion. The length of the middle portion approximates the wall in which the thickness of the defect to be occluded is formed. The center of at least one of the expanded diameter portions may be concentric with or offset relative to the center of the middle portion, thereby allowing occlusion of a variety of septal defects including membranous type ventricular septal defect, while providing a retention skirt of sufficient size to securely close the abnormal opening in the septum. As mentioned above, each braided end of the device is held together with a clamp. The clamps may be recessed into the expanded diameter portion of the device, thereby reducing the overall length dimension of the device and creating a low profile occluder.

In another embodiment of the Kotula et al. invention described in the '261 patent, the medical device is generally bell-shaped, having an elongate body, a tapered first end, and a larger flanged second end. The second end has a fabric disc which will be oriented generally perpendicular to an axis of a channel when deployed therein. The clamps, which hold together the braided strand ends, are recessed toward the center of the "bell" providing a low-profile device having a reduced overall height dimension.

The ability of the devices described in the Kotula et al. '261 patent to occlude abnormal openings in a vascular organ depend upon the pick size of the braided structure which, in turn, depends upon the number of wire strands used in the braid. However, a practical limit exists on just how many such strands can be braided. For example, if 72 bobbins are used on the braiding machine, the resulting pick size is such that a prolonged period of time must elapse before total thrombosis takes place and blood flow through the device is totally occluded. Even with 144 bobbins, blood flow is not immediately stemmed. If the pick size were effectively halved by doubling the number of bobbins on the braiding machine to 288, occlusion would occur somewhat instantaneous upon placement of the medical device in the abnormal opening. However, the resulting braiding machine becomes impractical from a size and cost standpoint.

As a way of reducing the time required to achieve total occlusion, the Kotula et al. '261 patent teaches the concept of filling the interior of the medical device with an occluding fiber or an occluding fabric, such as a polyester fabric. This occluding fiber material or fabric is generally hand sewn in place, which adds significantly to the manufacturing cost of the medical devices. Perhaps more importantly, adding polyester fiber or fabric in the interior of the device interferes with the ability to reduce the effective diameter of the device upon stretching prior to loading the device into the lumen of a delivery catheter. It should be recognized that by reducing the size of the delivery catheter, it can be used with smaller patients.

Thus, a need exists for a way to form a collapsible medical device for occluding abnormal openings in a vascular organ which provides rapid occlusion following delivery and placement thereof and which does not require the addition of an occluding fabric placed within the interior of the medical device as taught by the prior art.

Another limitation of the bell-shaped occlusion device described in the Kotula et al '261 patent regards its use in occluding a Patent Ductus Arteriosus (PDA) This passage way between the pulmonary artery and the aorta is variable in diameter and length and the passageway is not always perpendicular to the connected vessels. The design of the bell-shape occlusion device is such that the rim at one end of the device placed in the higher pressure aortic side may project into the aorta when the passage is not perpendicular to the aortic wall. The bell-shaped design also does not accommodate passageway length and route variation ideally and it is possible for the device to partially extrude out of the PDA. A further limitation is that the device must be delivered from the more difficult to reach pulmonary artery side of the PDA. This is due to the arterial sheath size being larger than the femoral artery in young patients. For infants, there is a need for a PDA occluder design that is low in profile that can be delivered through a 4 French catheter that allows for a venous delivery in premature infants and an arterial approach in premature infants weighing more than 1.5-2 kg. The advantage of a venous approach for PDA closure is to potentially treat infants as small a 1 kg. The advantage of an arterial approach in slightly larger premature infants is that both angiography and device implant can take place from a common access point in the femoral artery.

There is also a need for an improved occlusion device (occluder) for closing the PDA that allows for: improved security of placement; improved accommodation of diameter, length, and pathway variation; minimal projection into the flow stream of the pulmonary and aortic arteries; and for improved ease of placement from the aortic side by femoral artery access in addition to the previous pulmonary artery access.

In treating damaged or diseased heart valves such as the mitral or aortic valve, it is often necessary to surgically repair or replace the valve with a tissue or mechanical valve. These valves generally have a fabric cuff surrounding the valve at the base. The surgeon uses suture to sew tissue, adjacent the valve base, to the cuff to hold the valve in place. For a number of reasons, the suture may occasionally pull out from weak tissue or suture may break or suture may not have been sewn ideally. In any event this loss of connective tissue to the valve cuff results in open holes (para-valvular leak, PVL) along the cuff causing valve leakage and poor valve performance from regurgitation of blood between the ventricle and the atrium and a lowering of blood pressure. These open areas may be round, oval or crescent shaped and must be closed by surgical or other means. Today there is no ideal means of closing these valve leaks other than by surgery. Attempts have been made by physicians to deploy devices as herein described by the Kotula el al '261 patent but this device has not been ideal for such variable sized and shaped leaks. One of the most time consuming aspects of a percutaneous endoluminal approach to closing a PVL is locating the closure device in the hole along the valve cuff Since the current devices are not steerable, it would be preferable that the device be delivered over a guidewire that can be more easily directed across the leak prior to placing the device. An alternative approach would be placing the device through a steerable tip sheath.

Therefore, an additional need exists for a method for percutaneous treatment of para-valvular leaks by use of an improved occlusion device that can be easily delivered over a guide wire or by a steerable sheath, in a low profile catheter based delivery system and which easily accommodates the variety of leak passageway shapes and sizes typical of such valve leakage cases without interfering with valve leaflet function.

The present invention provides a readily manufacturable solution to the aforementioned problems inherent in the prior art as represented by the Kotula et al. '261 patent.

SUMMARY OF THE INVENTION

A collapsible medical device made in accordance with the present invention comprises multiple layers including an outer metal fabric surrounding at least one, and possibly two or more, inner metal fabric(s) wherein each of the outer and inner metal fabrics each comprise a plurality of braided metal strands exhibiting an expanded preset configuration. The collapsible medical device has proximal and distal ends each incorporating clamps for securing the plurality of braided strands that comprise the inner and outer metal fabrics together. It is to be understood that each of the several inner layers may have their ends clamped individually and separately from the ends of the strands comprising the outer layer. The clamps for securing the plurality of metal strands may be oriented outward to form the device ends or may alternatively be recessed inward from the functional ends of the device. The medical device is shaped to create an occlusion of an abnormal opening in a vascular organ when in its expanded preset configuration. The expanded preset configuration is deformable to a lesser cross-sectional dimension for delivery through a channel in a patient's body. Both the outer and inner metal fabrics have a memory property such that the medical device tends to return to the expanded preset configuration when unconstrained. For example, by braiding the inner metal fabric(s) so as to have a greater number of braided metal strands than are provided in the outer metal fabric and of a smaller wire diameter, the resulting device is still readily deformable to a lesser cross-sectional dimension for delivery through a channel in a patient's body, yet the increase in the total number of metal strands comprising the outer and inner metal fabrics result in a device that provides more immediate occlusion and does not require a sewn-in occluding fabric. For example, the outer braided metal fabric may have, say, 72 strands; each of a first diameter while the inner metal fabric may be braided from 144 strands, each of a smaller diameter than the diameter of the strands in the outer fabric layer. The outer metal fabric can also be braided from 144 or more strands.

In alternative embodiments the layers may be reversed in that the innermost layer may have fewer braided wires of larger diameter than the layers surrounding the inner layer. In another embodiment the layer with fewer wires of larger diameter may be between the inner and outermost layer. In still another embodiment the layers may all have the same number of wires with the same or different wire diameters. In yet another variation the layers may all have the same diameter of wires with the same of different number of wires in each layer.

In other embodiments the various layers have different pre-set shapes in concentric co-axial arrangement. In another embodiment the inner layers are side by side instead of coaxial with the outer layer. In still another embodiment an outer layer, that defines a pre-shaped but conformable volume, surrounds a concentric very much longer braid, pre set into a bead & chain type shape. In this embodiment the internal beaded chain braid is inserted into the outer braid volume to fill the volume and cause the volume to take the shape of the cavity it is placed in. The filled volume results in quick hemostasis due to high metal density while maintaining a small diameter delivery profile.

BRIEF DESCRIPTION OF THE DRAWINGS

The foregoing features and advantages of the invention will become apparent to those skilled in the art from the following detailed description of a preferred embodiment, especially when considered in conjunction with the accompanying drawings in which like numerals in the several views refer to corresponding parts.

FIG. 1 is an enlarged, side elevation view of an ASD occluder incorporating the present invention;

FIG. 2 is an enlarged front elevation view of the device of FIG. 1;

FIG. 3 is an enlarged side elevation view of the device of FIG. 1 when longitudinally stretched;

FIG. 4 is a right end view of the device shown in FIG. 3;

FIG. 5 is an enlarged, side elevation view of a PDA occluder incorporating the present invention;

FIG. 6 is a right end view of the device of FIG. 5;

DETAILED DESCRIPTION OF THE PREFERRED EMBODIMENTS

Figure 7:
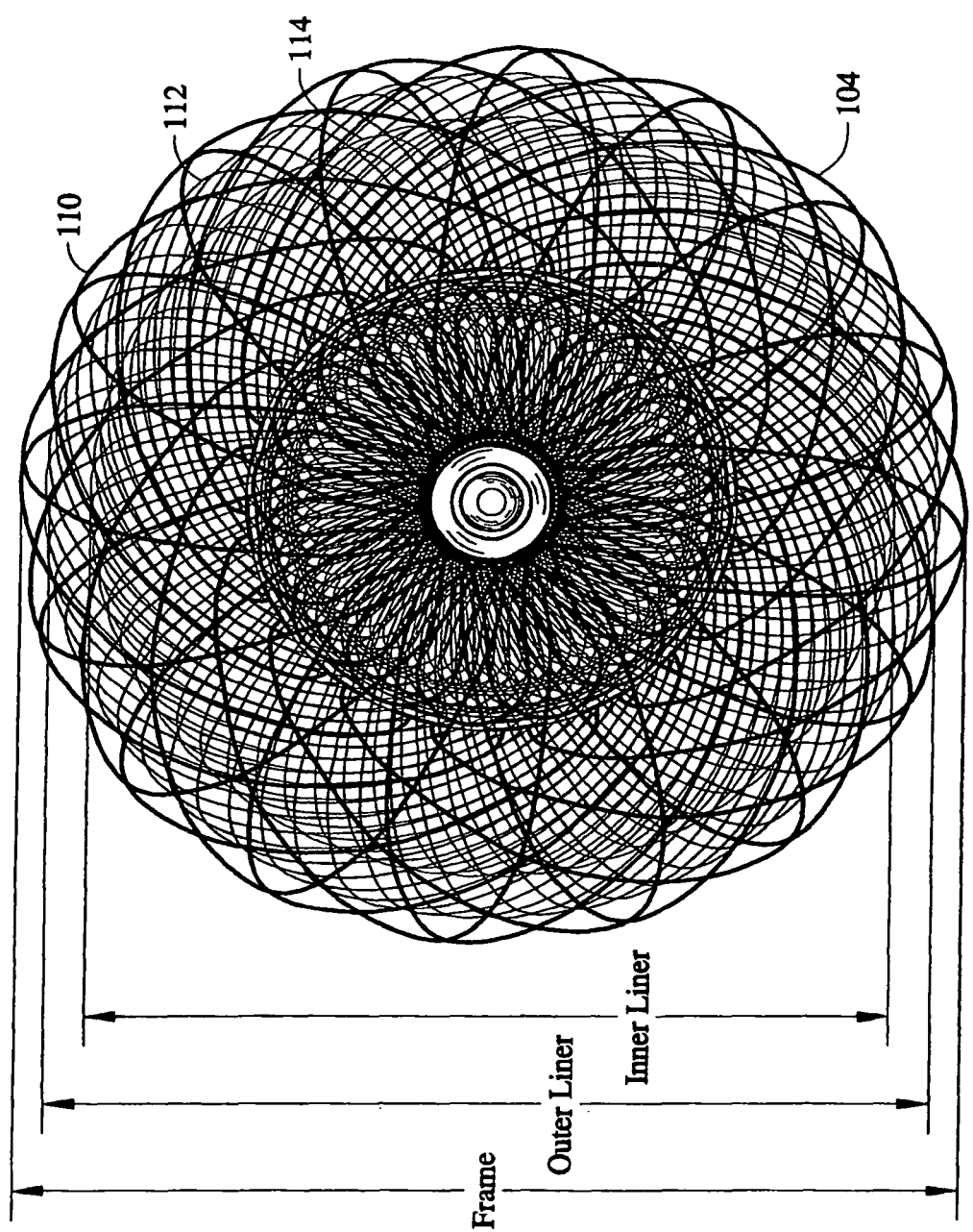
FIG. 7 is a greatly enlarged view like that of FIG. 6.

The present invention provides a percutaneous catheter directed occlusion device for use in occluding an abnormal opening in a patients' body, such as an Atrial Septal Defect (ASD), a ventricular septal defect (VSD), a Patent Ductus arteriosus (PDA), a Patent Foramen Ovale (PFO), and the like. It may also be used in fabricating a flow restrictor or an aneurysm bridge or other types of occluders for placement in the vascular system. In forming a medical device, via the method of the invention, a planar or tubular metal fabric is provided. The planar and tubular fabrics are formed of a plurality of wire strands having a predetermined relative orientation between the strands. The tubular fabric has metal strands which define two sets of essentially parallel generally helical strands, with the strands of one set having a "hand", i.e. a direction of rotation, opposite that of the other set. This tubular fabric is known in the fabric industry as a tubular braid.

The pitch of the wire strands (i.e. the angle defined between the turns of the wire and the axis of the braid) and the pick of the fabric (i.e. number of wire crossovers per inch) as well as some other factors, such as the number of wires employed in a tubular braid and their diameter, are important in determining a number of properties of the device. For example, the greater the pick and pitch of the fabric, and hence the greater the density of the wire strands in the fabric, the stiffer the device will be for a given wire diameter. Having a greater wire density will also provide the device with a greater wire surface area, which will generally enhance the tendency of the device to occlude a blood vessel in which it is deployed. This thrombogenicity can be either enhanced by, e.g. a coating of a thrombolytic agent, or abated, e.g. by a coating of a lubricious, anti-thrombogenic compound. When using a tubular braid to form a device of the Kotula '261 patent, a tubular braid of about 4 mm in diameter with a pitch of about 50 degrees and a pick of about 74 (per linear inch) would seem suitable for fabricating devices capable of occluding abnormal openings of about 2 mm to about 4 mm in inner diameter. However, the occlusion may not be immediate.

A metal planar fabric is a more conventional fabric and may take the form of a flat woven sheet, knitted sheet or the like. In the woven fabric there are typically two sets of metal strands, with one set of strands being oriented at an angle, e.g. generally perpendicular (having a pitch of about 45 degrees), with respect to the other set. As noted above, the pitch and pick of the fabric (or, in the case of a knit fabric, the pick and the pattern of the knit, e.g. Jersey or double knits) may be selected to optimize the desired properties of the resulting medical device.

The wire strands of the planar or tubular metal fabric are preferably manufactured from so-called shape memory alloys. Such alloys tend to have a temperature induced phase change which will cause the material to have a preferred configuration which can be fixed by heating the material above a certain transition temperature to induce a change in the phase of the material. When the alloy is cooled back down, the alloy will "remember" the shape it was in during the heat treatment and will tend to assume that configuration unless constrained from so doing.

Without any limitation intended, suitable wire strand materials may be selected from a group consisting of a cobalt-based low thermal expansion alloy referred to in the field as ELGELOY, nickel-based high temperature high-strength "superalloys" commercially available from Haynes International under the trade name HASTELLOY, nickel-based heat treatable alloys sold under the name INCOLOY by International Nickel, and a number of different grades of stainless steel. The important factor in choosing a suitable material for the wire strands is that the wires retain a suitable amount of the deformation induced by a molding surface (as described below) when subjected to a predetermined heat treatment.

In the preferred embodiment, the wire strands are made from a shape memory alloy, NiTi (known as Nitinol) that is an approximately stoichiometric alloy of nickel and titanium and may also include other minor amounts of other metals to achieve desired properties. Handling requirements and variations of NiTi alloy composition are known in the art, and therefore such alloys need not be discussed in detail here. U.S. Pat. No. 5,067,489 (Lind) and U.S. Pat. No. 4,991,602 (Amplatz et al.), the teachings of which are incorporated herein by reference, discuss the use of shape memory NiTi alloys in guide wires. Such NiTi alloys are preferred, at least in part, because they are commercially available and more is known about handling such alloys than other known shape memory alloys. NiTi alloys are also very elastic and are said to be "super elastic" or "pseudoelastic". This elasticity allows a device of the invention to return to a preset expanded configuration following deployment.

When forming a medical device in accordance with the present invention, rather than having a single braided fabric layer, a plurality of appropriately sized pieces of tubular or planar metal fabric are appropriately layered with respect to one another and inserted into the same mold, whereby the fabric layers deform to generally conform to the shape of the cavities within the mold. The shape of the cavities is such that the plural metal fabric layers deform into substantially the shape of the desired medical device. The ends of the wire strands of the tubular or planar metal fabric layers should be secured to prevent the metal fabrics from unraveling. A clamp or welding, as further described below, may be used to secure the ends of the wire strands. The advantages of the present invention can also be achieved by heat-treating the inner and outer fabric layers separately and then inserting the inner layer or layers within the confines of the outer layer.

It is further contemplated that the inner and outer fabric layers may be heat-set into different geometries and then assembled, one within the other, or may be heat set together in different geometries. In such case the pitch of one braid may be selectively different from the other if the end wires of all layers are joined together at each end. Alternatively, the end wires of the multiple layers may be joined together at only one end of the device and the other end may have separate layer end connectors where one end connector floats relative to the other connector(s) at the same device end. This allows for the same pitch in all layers and accommodates the change in length that would occur when two different shapes are compressed (axially elongated) for delivery. It is also contemplated that one layer could be attached to another layer, by for example a suture, at selective points in a middle portion of the device and not be co joined at the multiple layer braid wire ends. Where different layers have different shapes and have different compressed axial lengths, the shorter axial length ends may be connected to one or both ends of the longer length braid by an elastic member(s). As will be further explained, FIGS. 12a-12f illustrates several examples of layers having different shapes and connections.

In the case of a tubular braid, a molding element may be positioned within the lumen of the braid prior to insertion into the mold to thereby further define the molding surface. If the ends of the tubular metal fabric have already been fixed by a clamp or welding, the molding element may be inserted into the lumen by manually moving the wire strands of the fabric layers apart and inserting the molding element into the lumen of the innermost tubular fabric. By using such a molding element, the dimensions and shape of the finished medical device can be fairly accurately controlled and ensures that the fabric conforms to the mold cavity.

The molding element may be formed of a material selected to allow the molding element to be destroyed or removed from the interior of the metal fabric. For example, the molding element may be formed of a brittle, frangible or friable material. Once the material has been heat-treated in contact with the mold cavities and molding element, the molding element can be broken into smaller pieces, which can be readily removed from within the metal fabric. If this material is glass, for example, the molding element and the metal fabric can be struck against a hard surface, causing the glass to shatter. The glass shards can then be removed from the enclosure of the metal fabric.

Alternatively, the molding element can be formed of a material that can be chemically dissolved, or otherwise broken down, by a chemical agent that will not substantially adversely affect the properties of the metal wire strands. For example, the molding element can be formed of a temperature resistant plastic resin that is capable of being dissolved with a suitable organic solvent. In this instance, the fabric and the molding element can be subjected to a heat treatment to substantially set the shape of the fabric in conformance with the mold cavity and molding element, whereupon the molding element and the metal fabric can be immersed in the solvent. Once the molding element is substantially dissolved, the metal fabric can be removed from the solvent.

Care should be taken to ensure that the materials selected to form the molding element are capable of withstanding the heat treatment without losing their shape, at least until the shape of the multiple fabric layers has been set. For example, the molding element could be formed of a material having a melting point above the temperature necessary to set the shape of the wire strands, but below the melting point of the strands forming the metal fabric layers. The molding element and the layers of metal fabric ultimately comprising the medical device can then be heat treated to set the shape of the metal fabric, whereupon the temperature can be increased to substantially completely melt the molding element, thereby removing the molding element from within the metal fabric. Those skilled in the art will appreciate that the shapes of the mold cavities and the molding elements may be varied in order to produce the medical device having a preselected size and shape.

It should be understood that the specific shape of a particular molding element produces a specific shape and other molding elements having different shape configurations may be used as desired. If a more complex shape is desired, the molding element and mold may have additional parts including a camming arrangement, but if a simpler shape is being formed, the mold may have few parts. The number of parts in a given mold and the shapes of those parts will be dictated almost entirely by the shape of the desired medical device to which the metal fabric will generally conform.

When the multiple layers of tubular braid, for example, are in their relaxed configuration, the wire strands forming the tubular braids will have a first predetermined relative orientation with respect to one another. As the tubular braids are compressed along their axis, the fabric layers will tend to flare out away from the axis conforming to the shape of the mold. When so deformed, the relative orientation of the wire strands of the metal fabric layers will change. When the mold is assembled, the outer and inner metal fabrics will generally conform to the molding surface of the cavity. The medical device has a preset expanded configuration and a collapsed configuration which allows the device to be passed through a catheter or other similar delivery device. The shape of the fabric layers generally defines the expanded configuration when they are deformed to generally conform to the molding surface of the mold.

Once the tubular or planar metal fabric layers are properly positioned within a preselected mold with the metal fabric layers generally conforming to the molding surface of the cavities therein, the fabric layers can be subjected to a heat treatment while they remain in contact with the molding surface. Heat-treating the metal fabric comprising the plural layers substantially sets the shapes of the wire strands from which they are braided in a reoriented relative position when the fabric layers conform to the molding surface. When the medical device is removed from the mold, the fabric layers retain the shape of the molding surfaces of the mold cavities to thereby define a medical device having a desired shape. This heat treatment will depend in large part upon the material of which the wire strands of the metal fabric layers are formed, but the time and temperature of the heat treatment should be selected to substantially set the fabric layers in their deformed state, i.e., wherein the wire strands are in their reoriented relative configuration and the fabric layers generally conform to the molding surface.

After the heat treatment, the device is removed from contact with the mold surfaces and will substantially retain its shape in a deformed state. If a molding element is used, this molding element can be removed as described above.

The time and temperature of the heat treatment can very greatly depending upon the material used in forming the wire strands. As noted above, one preferred class of materials for forming the wire strands are shape memory alloys, with Nitinol, a nickel titanium alloy, being particularly preferred. If Nitinol is used in making the wire strands of the fabric layers, the wire strands will tend to be very elastic when the metal is in its austenitic phase; this very elastic phase is frequently referred to as a super elastic or pseudo elastic phase. By heating the Nitinol above a certain phase transition temperature, the crystal structure of the Nitinol metal will tend to "set" the shape of the fabric layers and the relative configuration of the wire strands in the positions in which they are held during the heat treatment.

Suitable heat treatments of Nitinol wire to set a desired shape are well known in the art. Spirally wound Nitinol coils, for example, are used in a number of medical devices, such as in forming the coils commonly carried around distal links of guide wires and in forming other medical products known in the art. A wide body of knowledge exists for forming Nitinol in such devices, so there is no need to go into great detail here on the parameters of a heat treatment for the Nitinol fabric preferred for use in the present invention.

Briefly, though, it has been found that holding a Nitinol fabric at about 500 degrees centigrade to about 550 degrees centigrade for a period of about 1 to 30 minutes, depending upon the size of the mold and the stiffness of the device to be made will tend to set the fabric layers in their deformed state, i.e., wherein they conform to the molding surface of the mold cavities. At lower temperatures, the heat treatment time will tend to be greater and at higher temperatures the time will tend to be shorter. These parameters can be varied as necessary to accommodate variations in the exact composition of the Nitinol, prior heat treatment of the Nitinol, the desired properties of the Nitinol in the finished article, and other factors which will be well known to those skilled in this field.

Instead of relying on convection heating or the like, it is also known in the art to apply an electrical current to the Nitinol to heat it. In the present invention, this can be accomplished by, for example, connecting electrodes to opposed ends of the metal fabric layers. Resistance heating in order to achieve the desired heat treatment, which will tend to eliminate the need to heat the entire mold to the desired heat-treating temperature, can then heat the wire. The materials, molding elements and methods of molding a medical device from a tubular or planar metal fabric is further described in U.S. Pat. Nos. 5,725,552, 5,944,738 and 5,846,261 and assigned to the same assignee as the present invention, the entire disclosures of which are incorporated herein by reference.

Once a device having a preselected shape has been formed, the device may be used to treat a physiological condition of a patient. A medical device suitable for treating the condition, which may be substantially in accordance with one of the embodiments outlined below, is selected. Once the appropriate medical device is selected, a catheter or other suitable delivery device may be positioned within a channel in a patient's body to place the distal end of the delivery device adjacent the desired treatment site, such as immediately adjacent (or even within) the shunt of an abnormal opening in the patient's organ for example.

The delivery device (not shown) can take any suitable shape, but desirably comprises an elongate flexible metal shaft or hypotube or metal braided polymer tube having a threaded distal end for engagement with a threaded bore formed in the clamp of the medical device. The delivery device can be used to urge the medical device through the lumen of a catheter/sheath for deployment in a channel of a patient's body. When the medical device is deployed out the distal end of the catheter, the delivery device still will retain it. Once the medical device is properly positioned within the shunt of the abnormal opening, the shaft of the delivery device can be rotated about its axis to unscrew the medical device from the delivery means.

In one embodiment the occluder device, delivery catheter and catheter/sheath accommodate a coaxial guidewire that slideably passes through the device, end clamps and delivery catheter central lumen, and therefore helps guide the delivery device and outer catheter/sheath to the desired location. The guidewire may be delivered independently through the vasculature and across the targeted treatment location or may be extended partially distal to the distal end of the delivery device and catheter/sheath and advanced with the delivery device and catheter/sheath while the guidewire is manipulated to guide the occluder to the desired location. In another embodiment, the catheter/sheath is steerable to assist in placement of the delivery device and occluder.

By keeping the medical device attached to the delivery means, the operator can retract the device for repositioning relative to the abnormal opening, if it is determined that the device is not properly positioned within the shunt. A threaded clamp attached to the medical device allows the operator to control the manner in which the medical device is deployed out the distal end of the catheter. When the medical device exits the catheter, it will tend to resiliently return to a preferred expanded shape, which is set when the fabric is heat-treated. When the device springs back into this shape, it may tend to act against the distal end of the catheter effectively urging itself forward beyond the end of the catheter. This spring action could conceivably result in improper positioning of the device if the location of the device within a channel is critical, such as where it is being positioned in a shunt between two vessels. Since the threaded clamp can enable the operator to maintain a hold on the device during deployment, the spring action of the device can be controlled by the operator to ensure proper positioning during deployment.

The medical device can be collapsed into its reduced diameter configuration and inserted into the lumen of the catheter. The collapsed configuration of the device may be of any shape suitable for easy passage through the lumen of a catheter and proper deployment out the distal end of the catheter. For example, an ASD occluding device may have a relatively elongated collapsed configuration wherein the devices are stretched along their axes. This collapsed configuration can be achieved simply by stretching the device generally along its axis, e.g. by manually grasping the clamps and pulling them apart, which will tend to collapse the expanded diameter portions of the device inwardly toward the device's axis. A PDA occlusion device also operates in much the same fashion and can be collapsed into its collapsed configuration for insertion into the catheter by applying tension generally along the axis of the device. In this regard, these devices are not unlike "Chinese handcuffs", which tend to constrict in diameter under axial tension.

If the device is to be used to permanently occlude a channel in the patient's body, one can simply retract the catheter and remove it from the patient's body. This will leave the medical device deployed in the patient's vascular system so that it may occlude the blood vessel or other channel in the patient's body. In some circumstances, the medical device may be attached to a delivery system in such a manner as to secure the device to the end of the delivery means. Before removing the catheter in such a system, it may be necessary to detach the medical device from the delivery means before removing the catheter and the delivery means.

Although the device will tend to resiliently return to its initial expanded configuration, i.e., its shape prior to being collapsed for passage through the catheter, it should be understood that it might not always return entirely to that shape. For example, it may be desirable that the device has a maximum outer diameter in its expanded configuration at least as large as and preferably larger than, the inner diameter of the lumen of the abnormal opening in which it is to be deployed. If such a device is deployed in a vessel or abnormal opening having a small lumen, engagement with the lumen will prevent the device from completely returning to its expanded configuration. Nonetheless, the device would be properly deployed because it would engage the inner wall of the lumen to seat the device therein.

When the device is deployed in a patient, thrombi will tend to collect on the surface of the wires. By having a greater wire density and smaller flow passages between wires as afforded by the multiple layer construction of the present invention, the total surface area of the wires and flow resistance will be increased, increasing the thrombotic activity of the device and permitting it to relatively rapidly occlude the vessel in which it is deployed. It is believed that forming the occlusion device with the outermost layer being 4 mm diameter tubular braid whose strands are about 0.004 inch in diameter and having a pick of at least about 40 and a pitch of at least about 30 degrees and surrounding an inner tubular braid whose strands are about 0.001 inch and of the same pick and pitch will provide sufficient surface area to substantially completely occlude an abnormal opening or blood vessel of 2 mm to about 4 mm in inner diameter in a very short period of time of less than five minutes. If it is desired to increase the rate at which the device occludes, a third or forth concentrically disposed braided layer can be added. Additionally the device wires may be coated with a thrombogenic coating to aid in the occlusion rate.

Referring now to the drawings, a discussion of the embodiments of the medical device of the present invention will next be presented. FIGS. 1-4 illustrate a first preferred embodiment of a medical device 10 constructed in accordance with the present invention for correcting an atrial septal defect (ASD). With reference to FIGS. 1-4, the device 10 is shown greatly enlarged so that the multiple layers comprising the medical device can be viewed. The ASD device is in its relaxed, non-stretched state with two aligned disks 12 and 14 linked together by a short middle cylindrical section 16 (FIG. 3). It is proposed that this device 10 may also be well suited in occluding defects known in the art as patent foramen ovale (hereinafter PFO). Those skilled in the art will appreciate that a device of this configuration may also be suitable for use in a transcatheter closure during a Fenestrated Fontan's procedure. ASD is a congenital abnormality of the atrial septum characterized by structural deficiency of the atrial septum. A shunt may be present in the atrial septum, allowing flow between the right and left atrial chambers of the heart. In large defects with significant left to right shunts through the defect, the right atrium and right ventricle are volume overloaded and the augmented volume is ejected into a low-resistance pulmonary vascular bed.

Pulmonary vascular occlusive disease and pulmonary atrial hypertension develops in adulthood. Patients with secundum ASD with a significant shunt (defined as a pulmonary blood flow to systemic blood flow ratio of greater than 1.5) are operated upon ideally at two to five years of age or whenever a diagnosis is made in later years. With the advent of two dimensional echocardiography and Doppler color flow mapping, the exact anatomy of the defect can be visualized. The size of the defect as determined by balloon measurement will correspond to the selected size of the ASD device 10 to be used.

The device 10, shown in its unconfined or relaxed state in FIGS. 1 and 2, is adapted to be deployed within the shunt comprising an ASD or a PFO. For exemplary purposes, use of the device 10 in an ASD closure procedure is described in the Kotula '261 patent referenced above and those wishing further information are referred to that patent. Turning first to the constructional features of the device 10, the ASD occluder is sized in proportion to the shunt to be occluded. In the relaxed orientation, the metal fabric is shaped such that two disk like members 12 and 14 are axially aligned and linked together by the short cylindrical segment 16. The length of the cylindrical segment 16 when not stretched preferably approximates the thickness of the atrial septum, and ranges between 3 to 5 mm. The proximal disk 12 and distal disk 14 preferably have an outer diameter sufficiently larger than the shunt to prevent dislodging of the device. The proximal disk 14 has a relatively flat configuration, whereas the distal disk 12 is preferably cupped towards the proximal end slightly overlapping the proximal disk 14. In this manner, the spring action of the device 10 will cause the perimeter edge 18 of the distal disk to fully engage the sidewall of the septum and likewise an outer edge of the proximal disk 14 will fully engage an opposite sidewall of the septum. Perimeter edge 18 of disk 12 as well as the perimeter edge of disk 14 may alternatively be configured with a larger radius outer edge compared to that shown in FIG. 1, to diminish forces on the tissue abutting the device.

In accordance with the present invention, the device 10 comprises an outer braided layer 20, a first inner layer 22 and possibly an optional third and innermost layer 24, thereby significantly increasing the wire density without unduly increasing the stiffness of the device or its ability to assume a decreased outer diameter upon longitudinal stretching. Multiple inner layers may be used as needed.

The ends of the tubular braided metal fabric device 10 are welded or clamped together with clamps as at 26, to avoid fraying. The ends of all of the layers may be grouped together and secured by two clamps, one at each end or separate clamps can be applied on each end of the individual layers. Of course the ends may alternately be held together by other means readily known to those skilled in the art. The clamp 26 tying together the wire strands of the multiple layers at one end also serves to connect the device to a delivery system. In the embodiment shown in FIG. 1, the clamp 26 is generally cylindrical in shape and has a recess (not shown) for receiving the ends of the metal fabric to substantially prevent the wires comprising the woven fabric from moving relative to one another. The clamp 26 also has a threaded bore 28. The threaded bore is adapted to receive and engage a threaded distal end of a delivery device, such as a pusher wire.

The ASD occlusion device 10 of this embodiment of the invention can advantageously be made in accordance with the method outlined above. The outer layer 20 of device 10 is preferably made from a 0.004-0.008 inch diameter Nitinol wire strands, but lesser or greater diameter strands can be used as well. The braiding of the wire mesh comprising the outer layer may be carried out with 28 picks per inch at a shield angle of about 64 degrees using a Maypole braider with 72 wire carriers. The braided layers 22 and 24 may each comprise 144 strands of Nitinol wire of a diameter in a range of from 0.001 inch to 0.002 inch, braided at the same pitch. The stiffness of the ASD device 100 may be increased or decreased by altering the wire size, the shield angle, the pick rate, and the number of wire carriers or the heat treatment process. Those skilled in the art will recognize from the preceding discussion that the cavities of a mold must be shaped consistent with the desired shape of the ASD device. Also, it will be recognized that certain desired configurations may require that portions of the cavities be cammed. FIG. 3 illustrates the ASD device 10 in a somewhat longitudinally stretched state. The distance separating the distal and proximal disks 12 and 14 is preferably equal or slightly less than the length of the cylindrical segment 16. The cup shape of each disk 12 and 14, ensures complete contact between the outer edge of each disk 12 and 14 and the atrial septum. Upon proper placement, a new endocardial layer of endothelial cells forms over the occlusion device 10, thereby reducing the chance of bacterial endocarditic and thromboembolisms.

The distance separating the disks 12 and 14 of occluding device 10 may be increased to thereby provide an occluding device suitable for use in occluding a channel within a patient's body, having particular advantages in use as a vascular occlusion device. The device 10 includes a generally tubular middle portion 16 and a pair of expanded diameter portions 12 and 14. The expanded diameter portions are disposed at either end of the generally tubular middle portion. The relative sizes of the tubular middle section 16 and the expanded diameter portions 12-14 can be varied as desired. The medical device can be used as a vascular occlusion device to substantially stop the flow of blood through a patient's blood vessel. When the device 10 is deployed within a patient's blood vessel, it is positioned within the vessel such that its longitudinal axis generally coincides with the axis of the vessel segment in which it is being inserted. The dumbbell shape is intended to limit the ability of the vascular occlusion device to turn at an angle with respect to the axis of the blood vessel to ensure that it remains in substantially the same position in which the operator deploys it within the vessel.

In order to relatively strongly engage the lumen of the blood vessel, the maximum diameter of the expanded diameter portions 12-14 should be selected so that it is at least as great as the diameter of the lumen of the vessel in which it is to be deployed and is optimally slightly greater than that diameter. When it is deployed within the patient's vessel, the vascular occlusion device will engage the lumen at two spaced apart locations. The device is desirably longer along its axis than the dimensions of its greatest diameter. This will substantially prevent the vascular occlusion device 10 from turning within the lumen at an angle to its axis, essentially preventing the device from becoming dislodged and tumbling along the vessel within the blood flowing through the vessel.

The relative sizes of the generally tubular middle portion 16 and expanded diameter portions 12-14 of the vascular occlusion device can be varied as desired for any particular application by appropriate selection of a mold to be used during the heat setting of the device. For example, the outer diameter of the middle portion 16 may range between about ¼ and about ⅓ of the maximum diameter of the expanded diameter portions and the length of the middle portion 16 may comprise about 20% to about 50% of the overall length of the device 10. Although these dimensions are suitable if the device is to be used solely for occluding a vascular vessel, it is to be understood that these dimensions may be varied if the device is to be used in other applications, such as a ventricular septal defect occluder (VSD).

The aspect ratio (i.e., the ratio of the length of the device over its maximum diameter or width) of the device 10 illustrated in this embodiment is desirably at least about 1.0, with a range of about 1.0 to about 3.0 being preferred and then aspect ratio of about 2.0 being particularly preferred. Having a greater aspect ratio will tend to prevent the device 10 from rotating generally perpendicularly to its axis, which may be referred to as an end-over-end roll. So long as the outer diameter of the expanded diameter portions 12-14 of the device 10 is large enough to seat the device fairly securely against the lumen of the channel in which the device is deployed, the inability of the device to turn end-over-end will help keep the device deployed precisely where it is positioned within the patient's vascular system or in any other channel in the patient's body. Alternatively, having expanded diameter portions 12-14 which have natural relaxed diameters substantially larger than a lumen of the vessels in which the device is deployed should also suffice to wedge the device into place in the vessel without undue concern being placed on the aspect ratio of the device.

Referring next to FIGS. 5-7, there is shown generally a device 100 suitable for occluding a patent ductus arteriosus (PDA). PDA is essentially a condition wherein two blood vessels, the aorta and the pulmonary artery adjacent the heart, have a shunt between their respective lumens. Blood can flow directly between these two blood vessels through the shunt, resulting in cardiac failure and pulmonary vascular disease. The PDA device 100 has a generally bell-shaped body 102 and an outwardly flaring forward end 104. The bell-shaped body 102 is adapted to be positioned within the aorta to help seat the body of the device in the shunt. The sizes of the body 102 and the end portion 104 can be varied as desired during manufacture to accommodate different sized shunts. For example, the body 102 may have a diameter along its generally slender middle of about 10 mm and a length along its axis of about 25 mm. In such a medical device 100, the base of the body may flare generally radially outward until it reaches an outer diameter equal to that of the forward end 104 which may be on the order of about 20 mm in diameter.

The base 106 desirably flares out relatively rapidly to define a shoulder 108, tapering radially outwardly from the body 102. When the device 100 is deployed in a vessel, this shoulder 108 will abut the perimeter of the lumen being treated with higher pressure. The forward end 104 is retained within the vessel and urges the base of the body 102 open to ensure that the shoulder 108 engages the wall of the vessel to prevent the device from becoming dislodged from within the shunt.

A PDA occlusion device 100 of this embodiment of the invention can advantageously be made in accordance with the method outlined above, namely deforming multiple layers 110, 112 and 114 (FIG. 7) of generally concentrically oriented tubular metal fabric to conform to a molding surface of a mold and heat-treating the fabric layers to substantially set the fabric layers in their deformed state. With continued reference to the greatly enlarged view of FIG. 7, the outer layer 110 comprises a frame that defines the outer shape of the medical device 100. It is preferably formed from 72 or 144 braided strands whose diameters are in a range of from 0.003 to about 0.008 inch. The pitch of the braid may be variable. Within this frame is the layer 112 that forms an outer liner. It may also prove expedient to incorporate a third layer 114 as an inner liner. The outer and inner liners may be braided using 144 strands of a shape memory wire whose diameter may be 0.001 to 0.002 inch. The pitch of the braid in layers 112 and 114 should be the same. As noted above, the ends 116 and 118 of the braided layers should be secured in order to prevent the braids from unraveling. In the preferred embodiment, clamps 120 are used to tie together the respective ends of the wire strands on each end 116 and 118 of the tubular braid members forming the occlusion device 100. Alternatively, different clamps may be used to secure the ends of the metal strands of the outer fabric layer than are used to secure the ends of the metal strands of each of the inner layers. It is to be understood that other suitable fastening means may be attached to the ends in other ways, such as by welding, soldering, brazing, use of biocompatible cementious material or in any other suitable fashion. One or both clamps 120 of the outer layer may include a threaded bore 122 that serves to connect the device 100 to a delivery system (not shown). In the embodiment shown, the clamps 120 are generally cylindrical in shape and have a crimping recess for receiving the ends of the wire strands to substantially prevent the wires from moving relative to one another.

When using untreated NiTi fabrics, the strands will tend to return to their unbraided configuration and the braided layers 110, 112 and 114 can unravel fairly quickly unless the ends of the length of the braided layers that are cut to form the device are constrained relative to one another. The clamps 120 are useful to prevent the layers of braid from unraveling at either end. Although soldering and brazing of NiTi alloys has proven to be fairly difficult, the ends can be welded together, such as by spot welding with a laser welder. When cutting the fabric comprising the multiple layers 110, 112 and 114 to the desired dimensions, care should be taken to ensure that the fabric layers do not unravel. In the case of tubular braids formed of NiTi alloys, for example, the individual strands will tend to return to their heat set configuration unless constrained. If the braid is heat treated to set the strands in the braided configuration, they will tend to remain in the braided form and only the ends will become frayed. However, it may be more economical to simply form the braid without heat-treating the braid since the fabric will be heat treated again in forming the medical device.

Once the fabric is compressed so as to conform to the walls defining the mold interior, the fabric layers can be subjected to a heat treatment such as is outlined above. When the mold is open again the fabric will generally retain its deformed, compressed configuration. The formed device 100 can be collapsed, such as by urging the clamps 120 generally axially away from one another, which will tend to collapse the device 100 toward its axis. The collapsed device can then be attached to a delivery device, such as an elongated flexible push wire and passed through a delivery catheter for deployment in a preselected site in the patient's body. The use of the resulting device to occlude a PDA is the same as has been described in the Kotula '261 patent and need not be repeated here.

Because of the significant increase in the number of wire strands in the composite multi-layer structure, it is no longer necessary to incorporate a sewn-in polyester material in order to reduce the time required to establish total occlusion of a PDA. This not only reduces the cost of manufacture but also facilitates loading of the resulting device into a delivery catheter of a reduced French size. Reduced French size means ability to treat smaller patents which is a major advantage.

Figure 8:
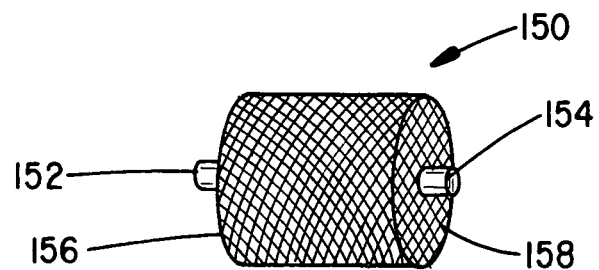
FIG. 8 shows a multi-layered vascular plug.
Figure 9:
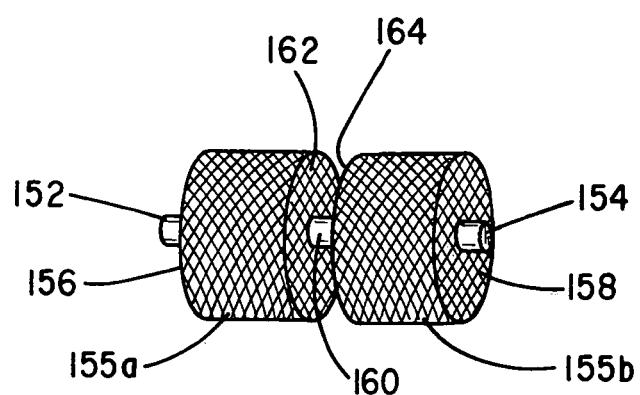
FIG. 9 shows the plug of FIG. 8 in combination with a center clamp.
Figure 10:
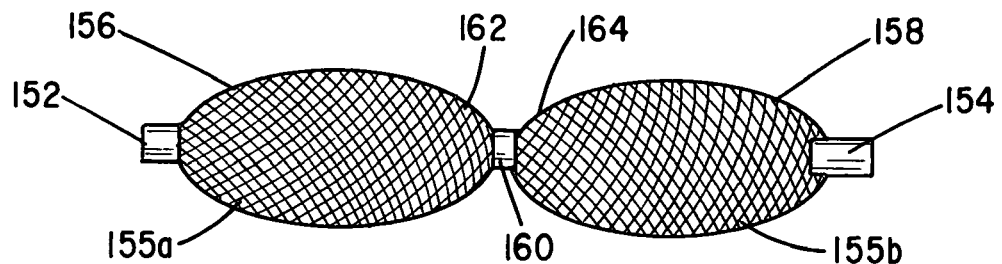
FIG. 10 shows an alternative multi-layered vascular plug.

FIGS. 8-10 show various vascular plug arrangements. These plugs are ideally suited for treating a variety of arterial-venous malformations and aneurysms. These plugs can also be used to block blood flow to a tumor or lesion. Likewise, these plugs can be used to bloc fluid flow through a portion of the vasculature of the body in connection with the treatment of other medical conditions.

Each embodiment shown in FIGS. 8-10 has a multi-layered braided structure 150, i.e., two or more layers of braided fabric. When the multi-layered braided structure has a tubular shape, a pair of end clamps 152 and 154 are provided to prevent the multi-layered braided structure from unraveling. Those skilled in the art will recognize that only a single end clamp is required if the braids are in the form of a sack as opposed to having a tubular shape.

The embodiment shown in FIG. 8 has a cylindrical wall 155 with two faces 156 and 158 at the opposite ends. Generally speaking, when the device is in its expanded configuration as shown in FIG. 8, the cylindrical wall abuts the wall of the vessel in which the device is deployed to hold the device in place. The two faces 156 and 158 preclude fluid flow past the device.

In some treatment situations, it may be desirable to increase the number of faces to increase the ability of the device to block fluid flow past the device. FIGS. 9 and 10 show how this can be accomplished.

The device shown in FIG. 9 also has a cylindrical wall 155, a proximal face 156 and a distal face 158. The embodiment of FIG. 9 further provides an intermediate clamp 160 clamping an intermediate portion of the multi-braided material. This divides the cylindrical wall into two sections 155*a* and 155*b* and forming two additional faces 162 and 164. When the device of FIG. 9 is deployed, the two sections 155*a* and 155*b* of cylindrical wall 155 still abuts the vessel wall to hold the device in place yet fluid must to traverse all for faces (namely faces 156, 158, 162 and 164) to flow past the device. The reduction in flow provided by the two additional faces 162 and 164 can result in faster clotting.

FIG. 10 shows the same basic structure as FIG. 9. The primary difference is that the application of the intermediate clamp 160 results in the two sections 155*a* and 155*b* having a bulbous rather than a cylindrical form. The widest part of sections 155*a* and 155*b* still engage the vessel wall and hold the device in place after deployment. There are also still four faces (156, 158, 162 and 164) even though they are curved as opposed to flat as shown in FIG. 9.

The intermediate clamp 160 can be made of any suitable material. Suture thread has proven to be effective. The two end clamps 152 and 154 are preferably made of a radiopaque material so they can easily be visualized using, for example, a fluoroscope. The intermediate clamp can be made of such material as well. Also, additional intermediate clamps can be added to further increase the number of faces. For example, if two intermediate clamps are used, a total of six faces would be present. With each additional clamp, two additional faces are provided.

Also, when the multi-layered braided structure (or at least one of the layers thereof) is made of a super elastic or shape memory material, it may be possible to eliminate the intermediate clamps and instead mold the device to have such a shape (e.g., a shape such as that shown in FIG. 8) when fully deployed and in its expanded preset configuration. Of course, all such embodiments, including those shown in FIGS. 8-10, are deformable to a lesser cross-sectional dimension for delivery through a catheter.

An alternative improved embodiment for the treatment of Patent Ductus Arteriosus (PDA) is shown is FIGS. 11*a*-11*d*. The following dimensions are given in relation to the typical size range for PDA pediatric passageways and not intended as a limitation. The PDA occlusion device 200 of this embodiment of the invention can advantageously be made in accordance with the method outlined above, namely deforming multiple layers 210, and 212 of generally concentrically oriented tubular metal fabric to conform to a molding surface of a mold and heat-treating the fabric layers to substantially set the fabric layers in their deformed state. The at least two layers of braid in this device have the same molded shape. The occlusion device 200 has two disks 202, 204, one at each end that has an outer portion, starting at diameter C and extending to diameter B, tapered toward the device center at an angle F that ranges from 20 to 40 degrees, preferably 30 degrees. Each disk has a central portion 206 that is perpendicular to the device 200 central axis and extends outward to a diameter C that ranges from 3 mm to 6 mm. Each disk is a mirror image of the other disk with an outer diameter B that ranges from 9 mm to 12 mm. The disks are thin with the disk wall essentially little more than the thickness of the 2 layers formed back to back, ranging from 0.005 to 0.010 inch, preferably 0.007 inch or a double wall thickness (4 layers) of 0.014 inch.

The device 200 includes a central cylindrical portion 214 of diameter C which ranges from 2 mm to 6 mm. The length of the cylindrical central section A, ranges from 2 mm to 8 mm. Between the disks at each end and the central cylindrical portion is a very reduced diameter E which ranges from 1 mm to 2 mm, preferably 1 mm (or a tightly bunched group of wires). The ratio of the large disk diameter B to the small diameter E ranges from 6 to 12.

This high ratio provides the ability of the disks to conform (pivot) to a wide range of wall angles relative to the axis of the PDA. This conformability is shown in four examples in FIG. 11*c*-11*f*. FIG. 11*c* illustrates a condition where the disks 202, 204 are relatively parallel but at a substantial angle to the central section or device axis. The central section is elongated due to a smaller passage than anticipated and the elongation accommodates the lengthen passage between disks. In FIG. 11*d* the disks are non-parallel to accommodate the walls of the aorta and again the central section is elongated as it conforms to the passageway between the disks. FIG. 11*e* illustrates a device placed in a para-membranous VSD. In this case the device is shown conforming to a thin membrane at the upper portion of the defect and to the thicker septum in the bottom portion of the defect. The central section fully expands to shorten the distance between disks to aid in clamping force and to fill the defect. FIG. 11*f* shows a device placed in a tear through a ventricular septum. The device central section 214 elongates to fill the tear and the disks conform to the septum walls.

Figure 11A:
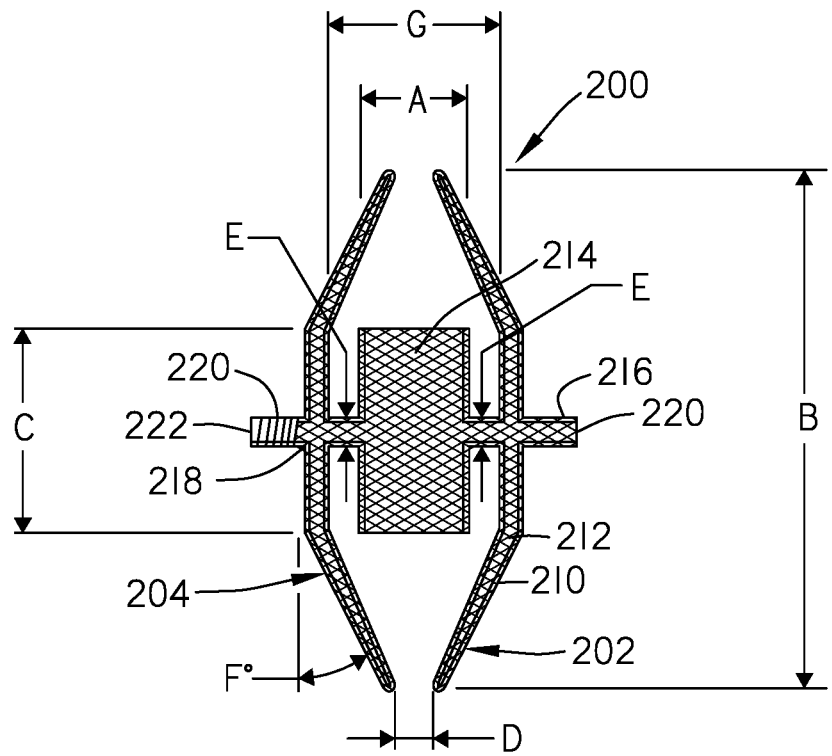
FIGS. 11a-11f are side and end views and cross-sectional views of an alternative embodiment occluder for treatment of the PDA or VSD with views of the occluder implanted in four varied anatomies.
Figure 11B:
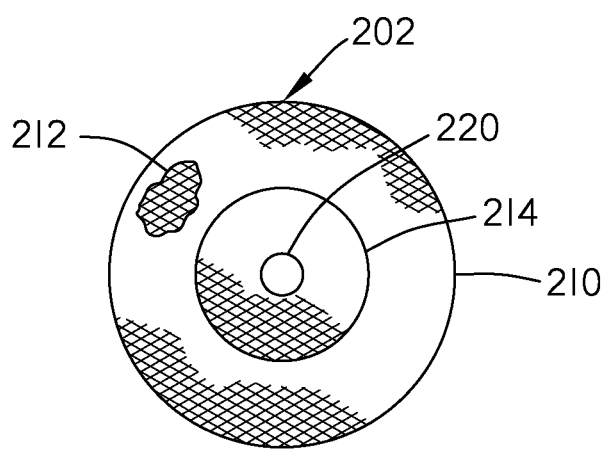
Figure 11C:
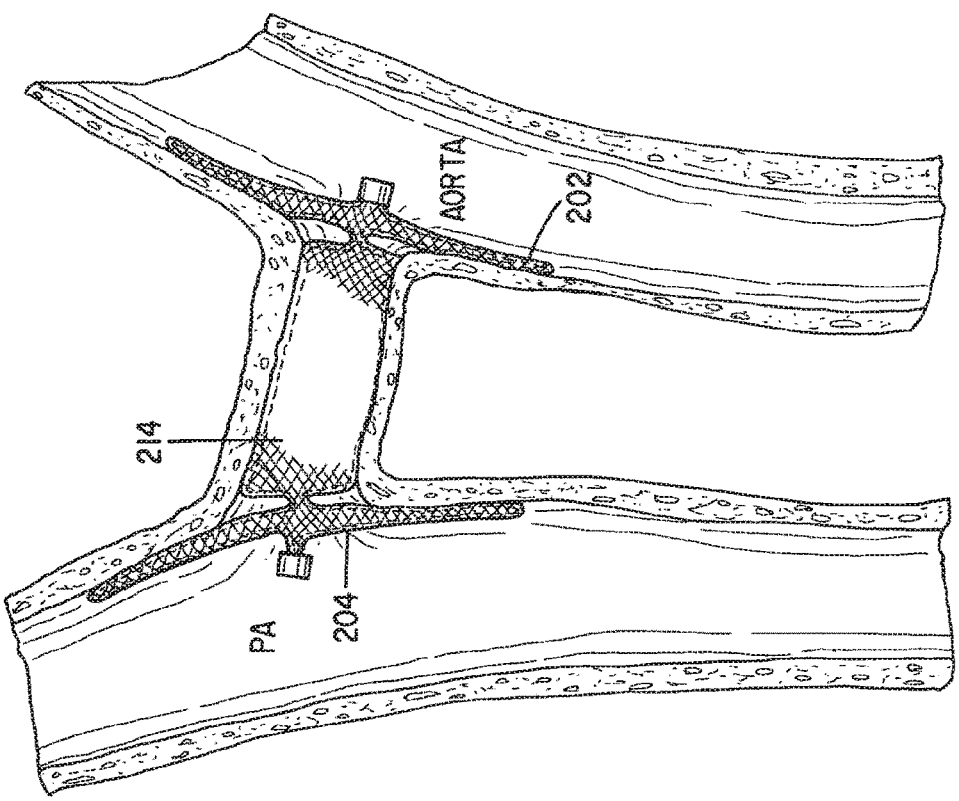
Figure 11D:
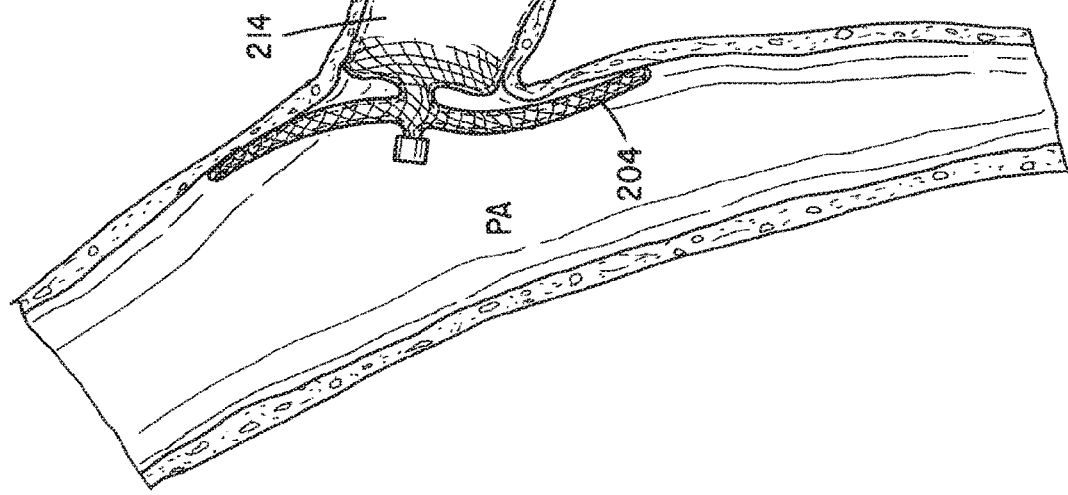
Figure 11F:
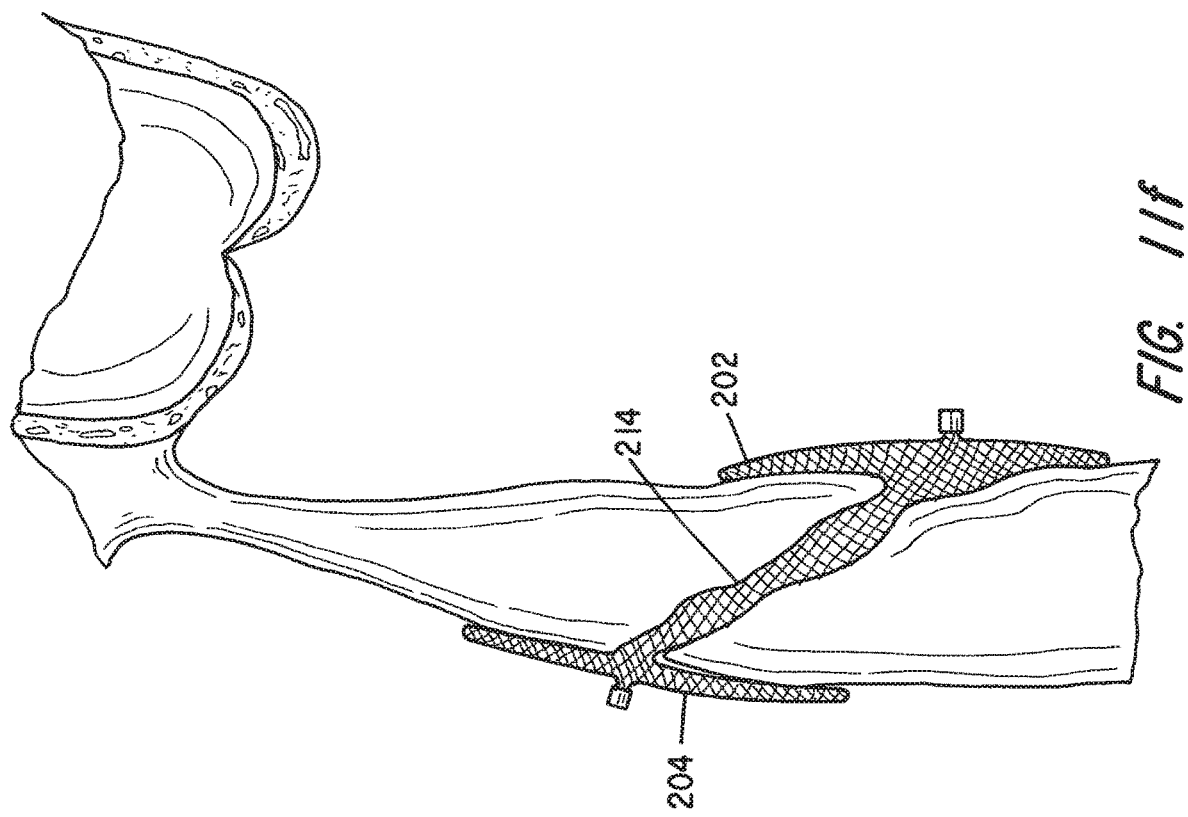
Figure 11E:
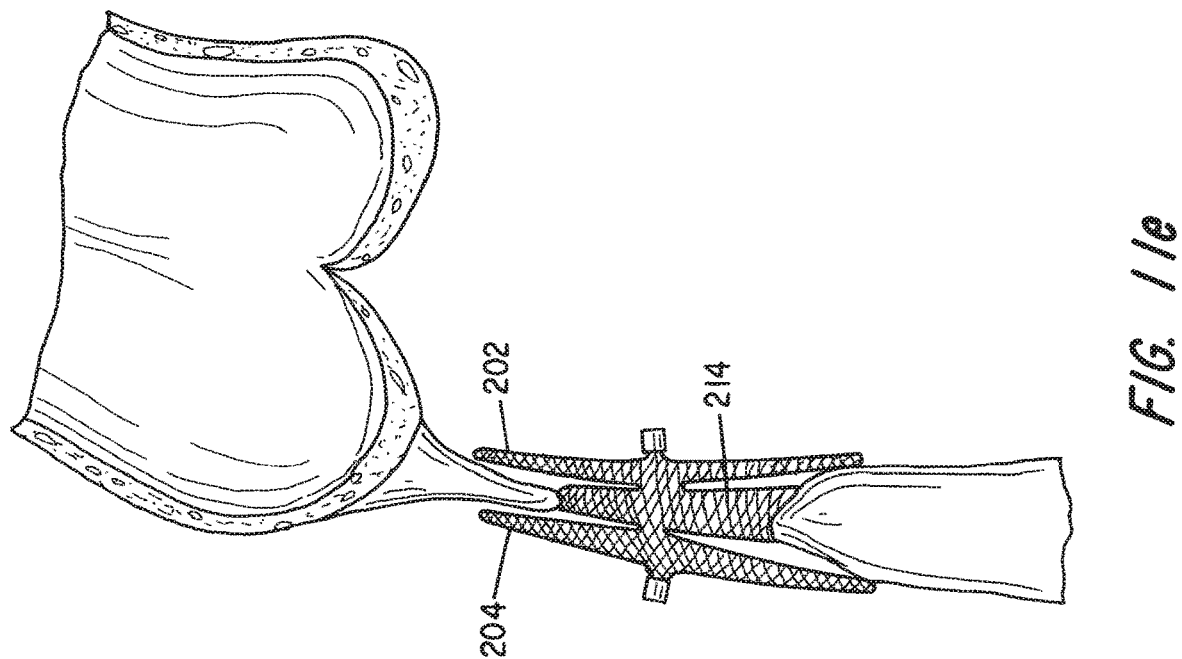

The ratio of diameters B to E and C to E, as defined in FIG. 11*a*, allows both the disks and central cylindrical portion to articulate about diameter E at an angle to the device axis and to conform more easily to vessel passageway variability and tissue irregularity at the disk contact area. Diameter C is selected to be a little larger (10-20%) than the passageway it is intended for, to provide some anchoring of the device. If the passageway is longer than anticipated the central portion can elongate to accommodate the longer length. The disks are spaced apart at there outermost point a distance D that ranges from 1 mm to 3 mm, preferably 1 mm. The distance between the inner surface of each disk, in the portion (C) perpendicular to the device central axis, is G and ranges from 3 to 7 mm, preferably 5 mm. The difference between distance G and A provides for passageway length variability and conformability to surface irregularities as well as acts like a spring to apply clamping pressure at each disk to the vessel to hold the device in place.

With continued reference to the greatly enlarged view of FIG. 11*a*, the outer layer 210 comprises a frame that defines the outer shape of the medical device 200. It is preferably formed from 72 braided strands whose diameters are in a range of from 0.001 to about 0.005 inch, preferably 0.0015 in. The pitch of the braid ranges from 45 to 70 degrees, preferably 60 degrees. Within this frame is the inner layer 212 having the same shape as outer layer 210. The inner layer is preferably braided using 144 strands of a shape memory wire whose diameter may be 0.001 to 0.003 in., preferably 0.0015 in. The pitch of the braid in layers 210 and 212 are preferably the same but can also be different without departing from the scope of the invention. As noted above, the ends 216 and 218 of the braided layers should be secured in order to prevent the braids from unraveling. In the preferred embodiment, clamps 220, made from platinum-iridium or stainless steel, are used to tie together the respective ends of the wire strands on each end 216 and 218 of the tubular braid members forming the occlusion device 200. The clamps 220 are preferably oriented outward from the disks as shown in FIG. 11*a* but may alternatively be recessed within the disk surface somewhat, although full recess of the clamps would require a recess in the central portion end walls and the disk walls to accommodate the clamp length. Alternatively, different clamps may be used to secure the ends of the metal strands of the outer fabric layer than are used to secure the ends of the metal strands of each of the inner layers. It is to be understood that other suitable fastening means may be attached to the ends in other ways, such as by welding, soldering, brazing, use of biocompatible cementious material or in any other suitable fashion. One or both clamps 220 may include a threaded bore 222 that serves to connect the device 200 to a delivery system (not shown). In the embodiment shown, the clamps 220 are generally cylindrical in shape and have a crimping recess for receiving the ends of the wire strands to substantially prevent the wires from moving relative to one another.

When using untreated NiTi fabrics, the strands will tend to return to their unbraided configuration and the braided layers 210, and 212 can unravel fairly quickly unless the ends of the length of the braided layers that are cut to form the device are constrained relative to one another. The clamps 220 are useful to prevent the layers of braid from unraveling at either end. Although soldering and brazing of NiTi alloys has proven to be fairly difficult, the ends can be welded together, such as by spot welding with a laser welder. When cutting the fabric comprising the multiple layers 210, and 212 to the desired dimensions, care should be taken to ensure that the fabric layers do not unravel. In the case of tubular braids formed of NiTi alloys, for example, the individual strands will tend to return to their heat set configuration unless constrained. If the braid is heat treated to set the strands in the braided configuration, they will tend to remain in the braided form and only the ends will become frayed. However, it may be more economical to simply form the braid without heat-treating the braid since the fabric will be heat treated again in forming the medical device.

In one embodiment of the occluder (not shown) designed to be advanced over a guidewire, the clamps 220 may comprise two concentric rings with the braid wires constrained between the rings, by either using the previous described methods or by swaging the outer ring against the wires and the inner ring. The use of an inner ring in the clamps 220, provides a central lumen for slidable passage of the guidewire. The treaded clamp can either use internal threads (inner ring) or external threads (outer ring), provided that a passage for the guidewire is present.

Once the fabric is compressed so as to conform to the walls defining the mold interior, the fabric layers can be subjected to a heat treatment such as is outlined above. When the mold is open again the fabric will generally retain its deformed, compressed configuration. The formed device 200 can be collapsed, such as by urging the clamps 220 generally axially away from one another, which will tend to collapse the device 200 toward its axis. The collapsed device can then be attached to a delivery device, such as an elongated flexible push wire and passed through a delivery catheter for deployment in a preselected site in the patient's body. The use of the resulting device to occlude a PDA is the same as has been described in the Kotula '261 patent and need not be repeated here.

Figure 12A:
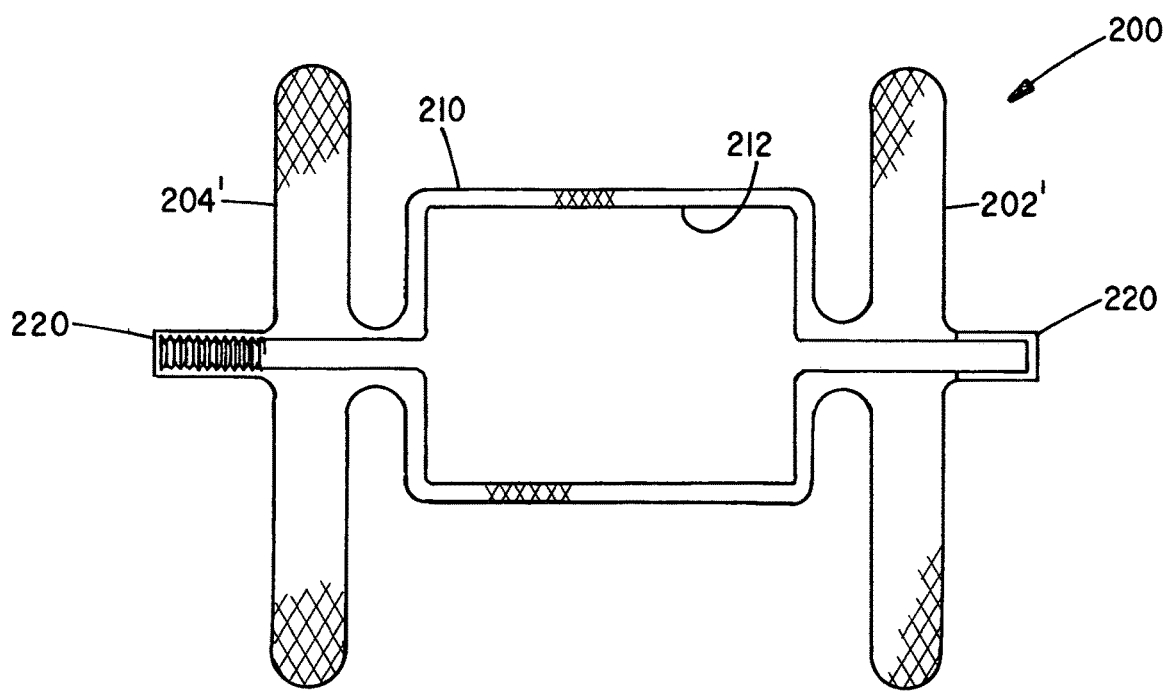
FIGS. 12a-12f show variations of design incorporating different shapes for each braid layer and means of connecting the layers & wire ends.
Figure 12B:
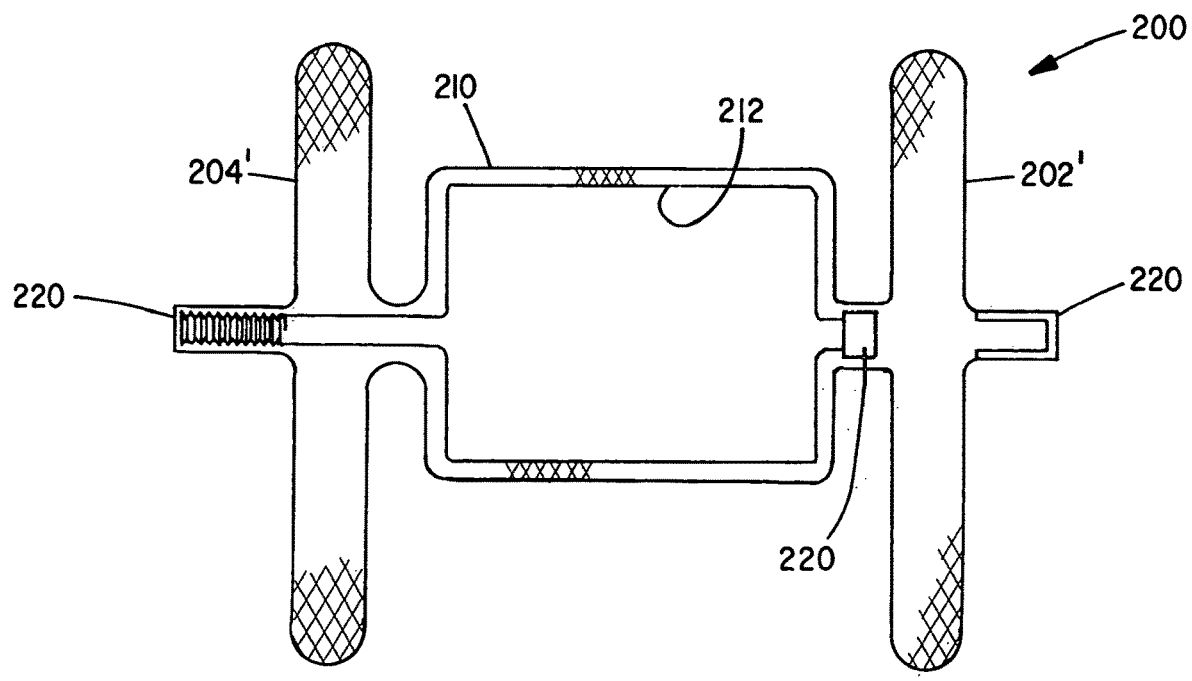
Figure 12C:
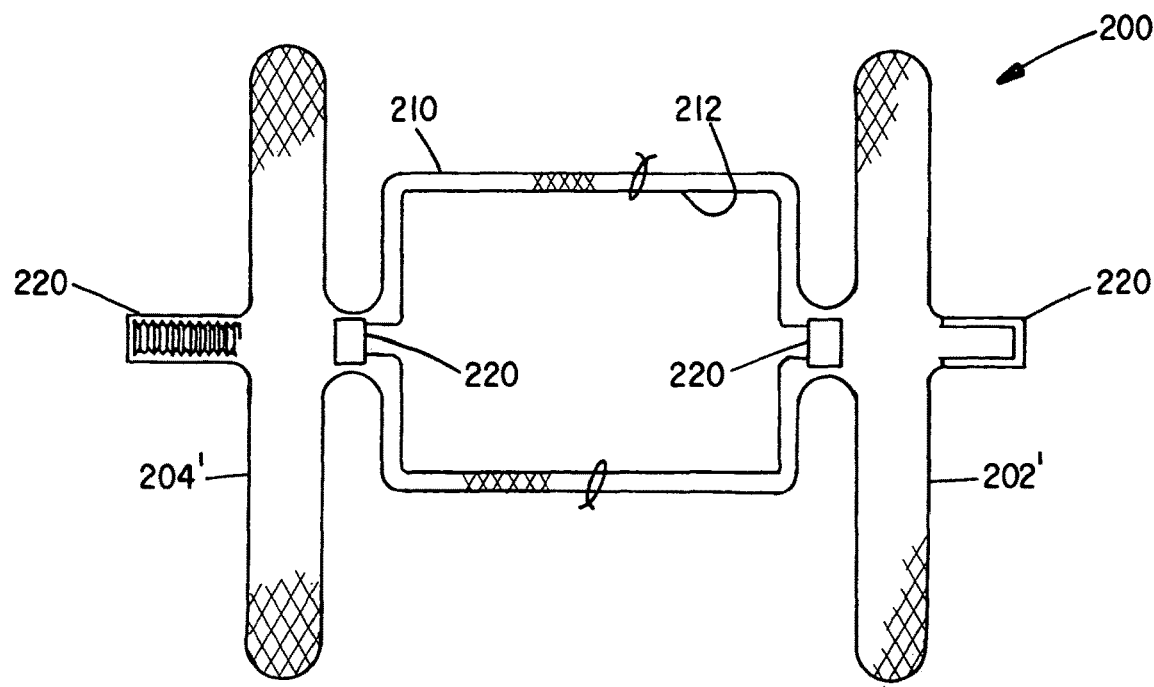
Figure 12D:
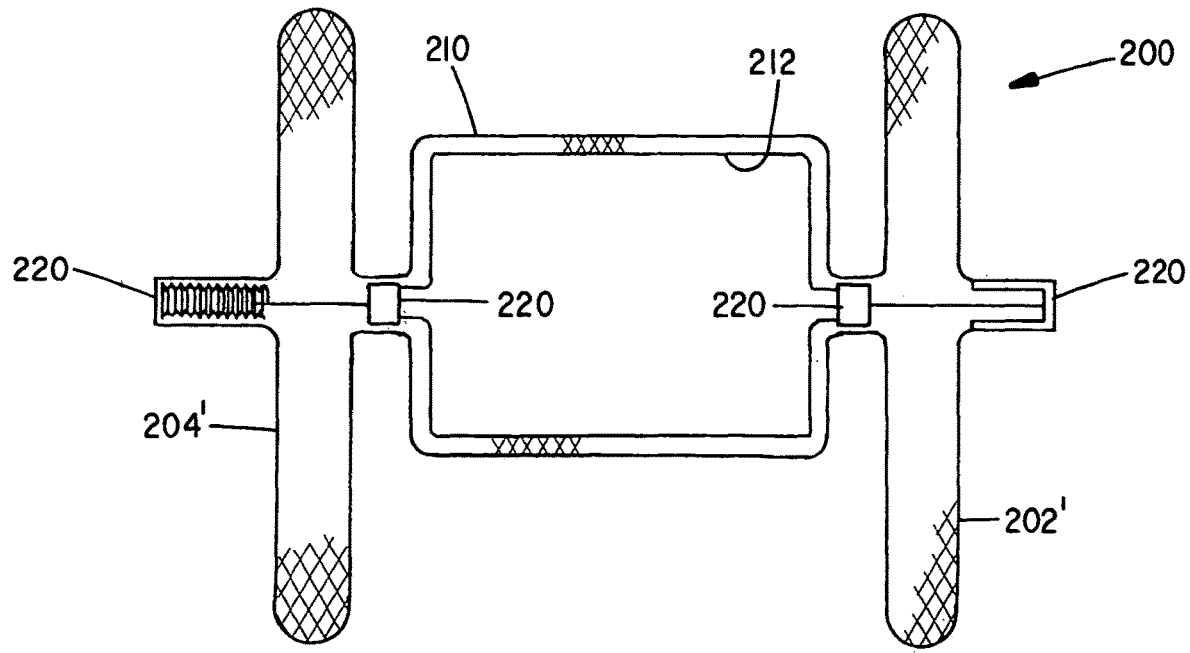
Figure 12E:
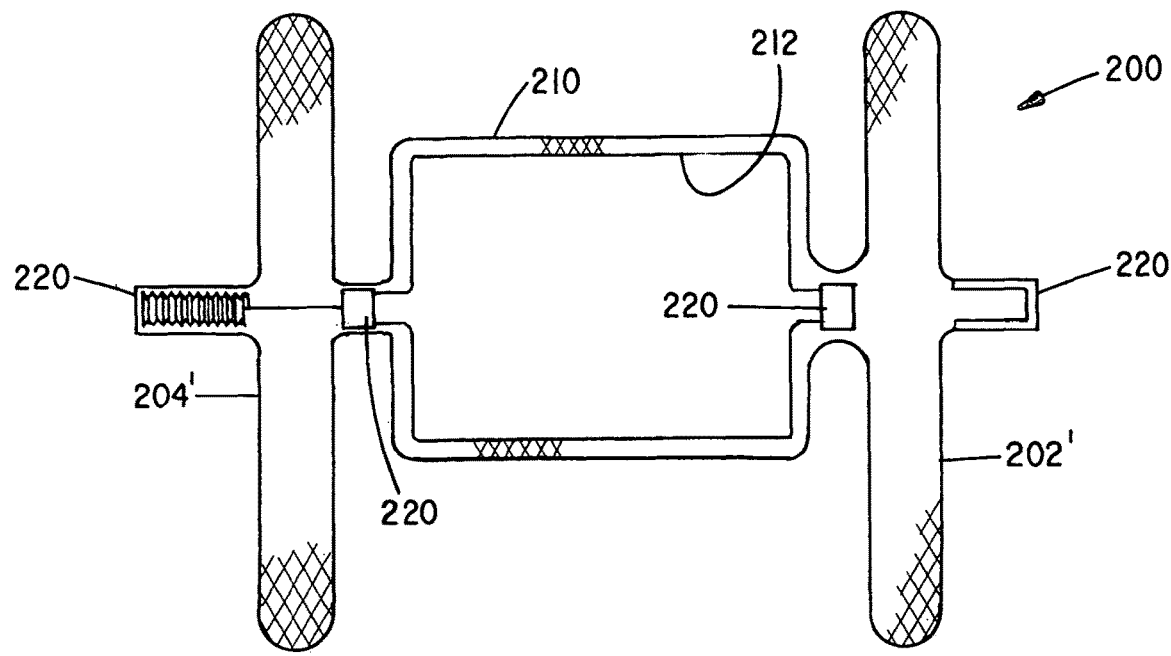
Figure 12F:
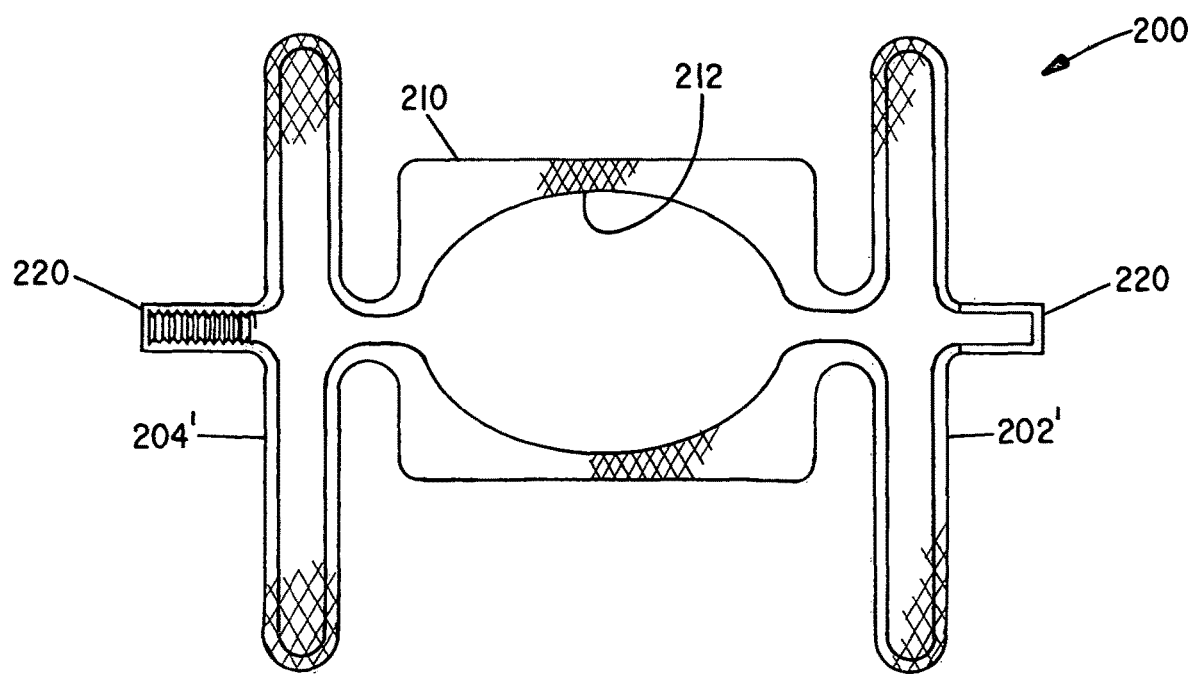

Other alternative embodiments are shown diagrammatically in FIGS. 12a-12f. Each of the designs incorporate the beneficial features, range of dimensions, fabric selection, etc., of the prior embodiments except as noted. In FIG. 12a the disks 202' and 204' are fabricated from a single layer folded back on itself, while the central portion is double layered. In this case the pitch of the inner layer would have to be increased relative to the outer layer so that both layers had the same collapsed length. This gives flexibility to the designer to have different characteristics in the disk portion relative to the central portion of the device. FIG. 12f shows an embodiment where the design is reversed to have double layers in the disk portion back to back, with a single layer in the central portion or a different shape for each layer in the central portion as shown.

FIG. 12b illustrates a design variation where the multiple braid layers have end wires connected at one end in a common clamp but where the inner layer at the opposite end has a clamp that free floats and is separate from the clamp for the outer layer. In this design there is freedom to have different compressed braid lengths so that the pitch may be varied as desired. The inner layer could also follow the shape of the outer layer in entirety if desired with a different pitch between layers.

In the embodiment of FIG. 12c the inner layer 212 is suspended by suture connectors between the layers and the end clamps of each layer are independent of each other.

In FIG. 12d the inner layer 212 has independent end clamps as in FIG. 12c, but rather than the layers connected by sutures, the layers 210 and 212 have their end clamps connected by elastic members, such as made from silicone rubber. FIG. 12e is similar to FIG. 12d except that the connector could be a non-elastomer such as suture or wire and may be connected optionally at only one set of end clamps. All embodiments shown in FIGS. 12a-12f have a relatively small diameter E in comparison to diameters B and C to maintain the articulation benefits. Diameters A, B, C and E are defined as in FIG. 11a. It is anticipated that the various optional characteristics, as shown in FIGS. 12a-12f, could be combined in any manner desired for any embodiment described herein.

Figure 13A:
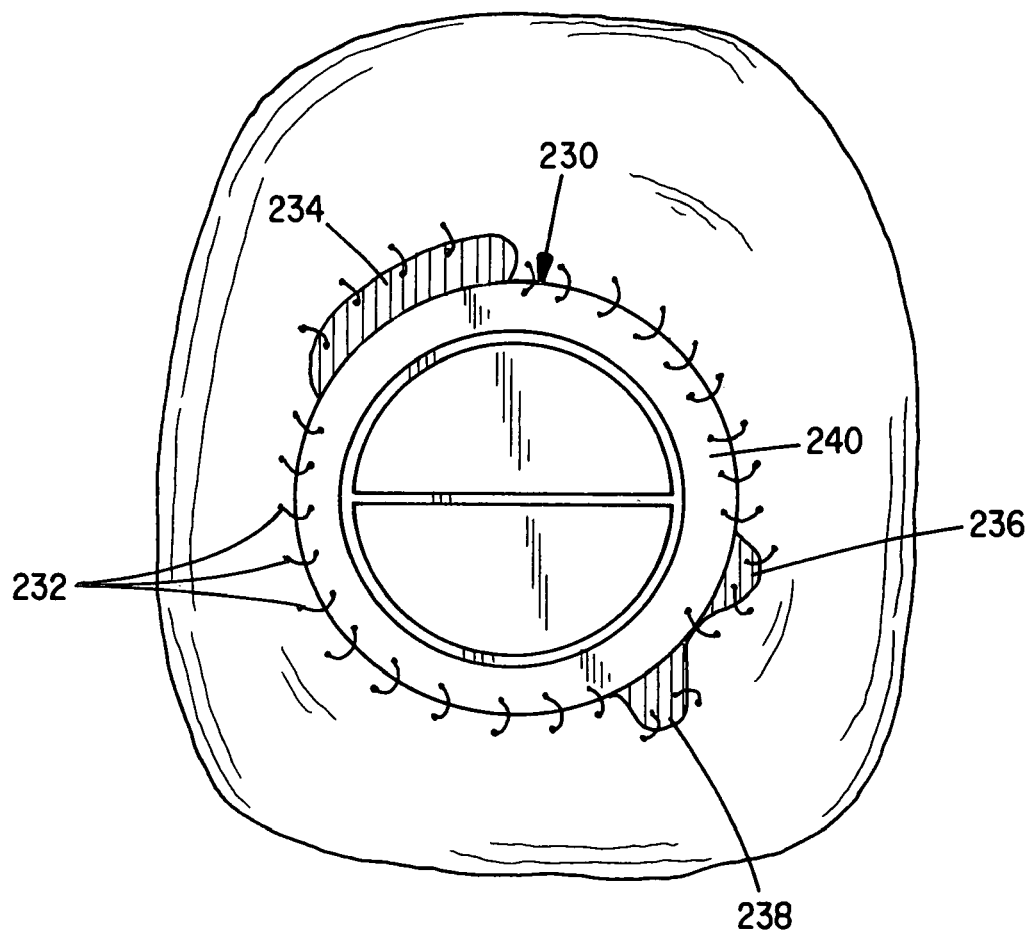
FIGS. 13a-13f are views of an example Para-Valvular Leak anatomy, and various optional occluder designs for treating PVL.

Various embodiments for treating Para-Valvular Leaks (PVL) are illustrated in FIGS. 13a-13f. FIG. 13a shows an artificial bi-leaflet valve sewn by suture 232 into a patient. Three cross-hatched areas 234, 236 and 238 along the valve cuff represent open areas where tissue has pulled away from the cuff from weak tissue or broken or loose sutures. These open areas allow blood to short circuit the valve and result in poor heart function and lower blood pressure. The invention herein is designed to close/occlude these PVLs such as are shown in FIGS. 13a-13f.

A PVL occlusion device 300 of this embodiment of the invention can advantageously be made in accordance with the method outlined above, namely deforming multiple layers 310, 312 of generally concentrically oriented tubular metal fabric to conform to a molding surface of a mold and heat-treating the fabric layers to substantially set the fabric layers in their deformed state. With continued reference to the greatly enlarged view of FIG. 13b-I, the outer layer 310 comprises a frame that defines the outer shape of the medical device 300. It is preferably formed from 144 braided strands whose diameters are in a range of from 0.0015 to about 0.0035 inch preferably 0.002 inch. The pitch of the braid may range from 45 to 70 degrees, preferably 60 degrees. Within this frame is the inner layer 312. It may also prove expedient to incorporate a third layer 314 (not shown) as an innermost liner. The inner layer may be braided using 144 strands of a shape memory wire whose diameter ranges from 0.001 to 0.002 inch, preferably 0.0015 inch. The pitch of the braid in layers 310 and 312 preferably are the same. As noted above, the ends 316 and 318 of the braided layers should be secured in order to prevent the braids from unraveling. In the preferred embodiment, clamps 320 are used to tie together the respective ends of the wire strands on each end 316 and 318 of the tubular braid members forming the occlusion device 300. Alternatively, different clamps may be used to secure the ends of the metal strands of the outer fabric layer than are used to secure the ends of the metal strands of each of the inner layers. It is to be understood that other suitable fastening means may be attached to the ends in other ways, such as by welding, soldering, brazing, use of biocompatible cementious material or in any other suitable fashion. One or both clamps 320 of the outer layer may include a threaded bore 322 that serves to connect the device 300 to a delivery system (not shown). In the embodiment shown, the clamps 320 are generally cylindrical in shape and have a crimping recess for receiving the ends of the wire strands to substantially prevent the wires from moving relative to one another.

When using untreated NiTi fabrics, the strands will tend to return to their unbraided configuration and the braided layers 310, and 312 can unravel fairly quickly unless the ends of the length of the braided layers that are cut to form the device are constrained relative to one another. The clamps 320 are useful to prevent the layers of braid from unraveling at either end. Although soldering and brazing of NiTi alloys has proven to be fairly difficult, the ends can be welded together, such as by spot welding with a laser welder. When cutting the fabric comprising the multiple layers 310, and 312 to the desired dimensions, care should be taken to ensure that the fabric layers do not unravel. In the case of tubular braids formed of NiTi alloys, for example, the individual strands will tend to return to their heat set configuration unless constrained. If the braid is heat treated to set the strands in the braided configuration, they will tend to remain in the braided form and only the ends will become frayed. However, it may be more economical to simply form the braid without heat-treating the braid since the fabric will be heat treated again in forming the medical device.

Figure 13B:
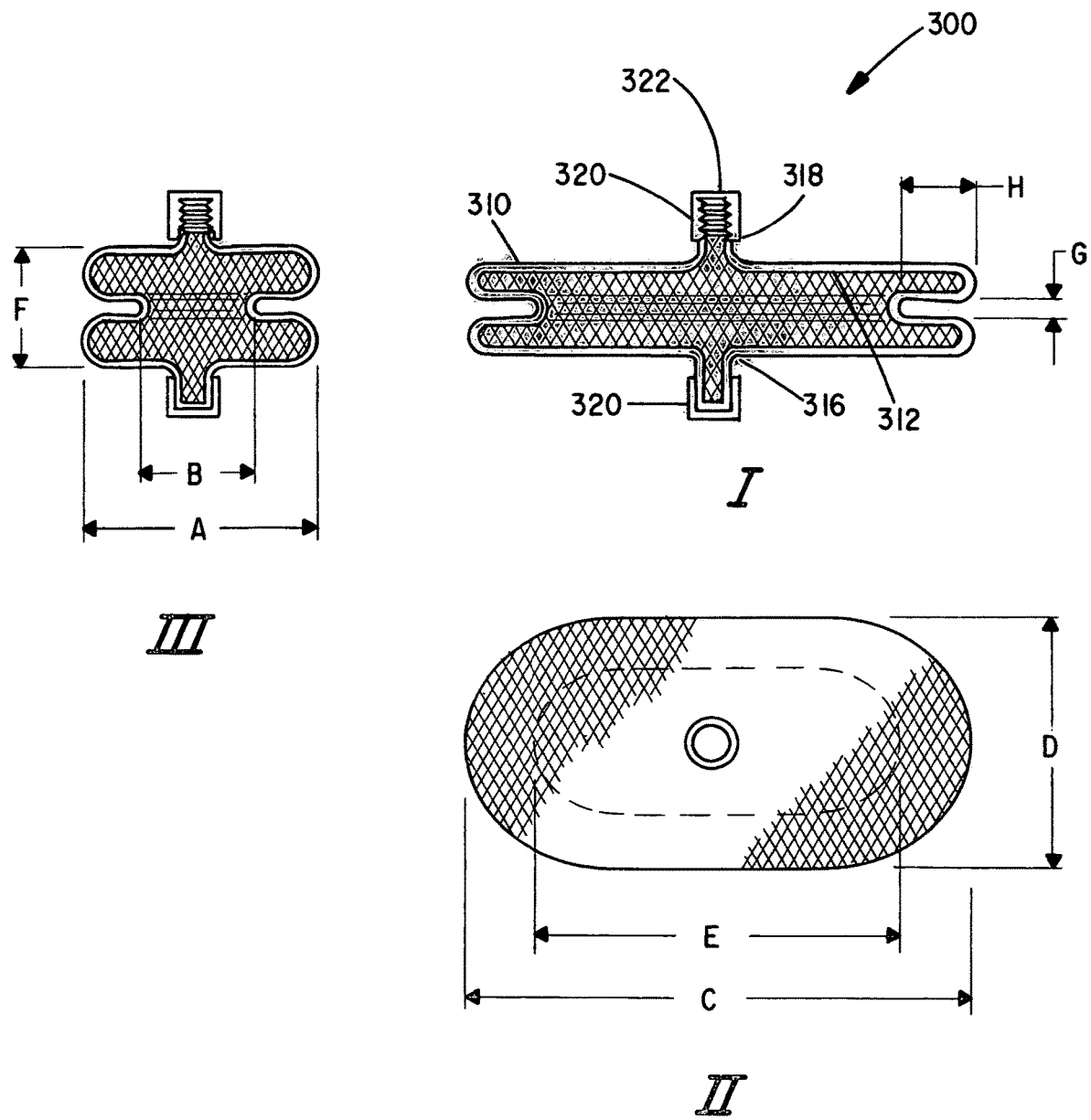
Figure 13D:
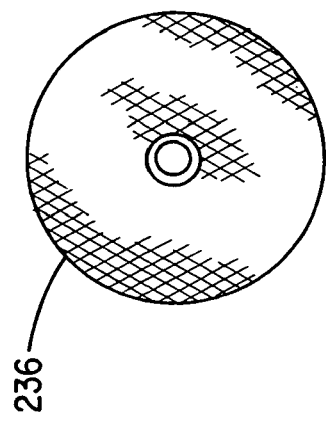
Figure 13C:
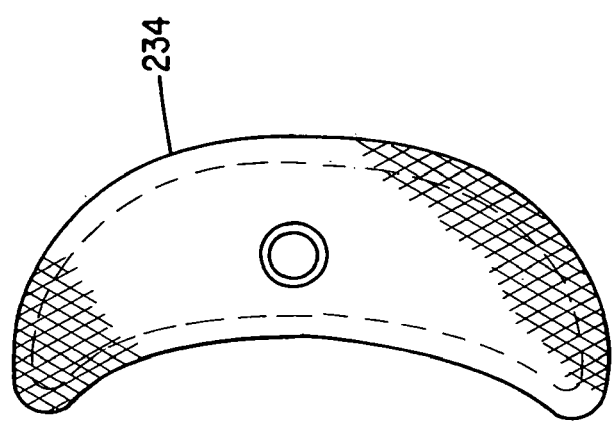
Figure 13E:
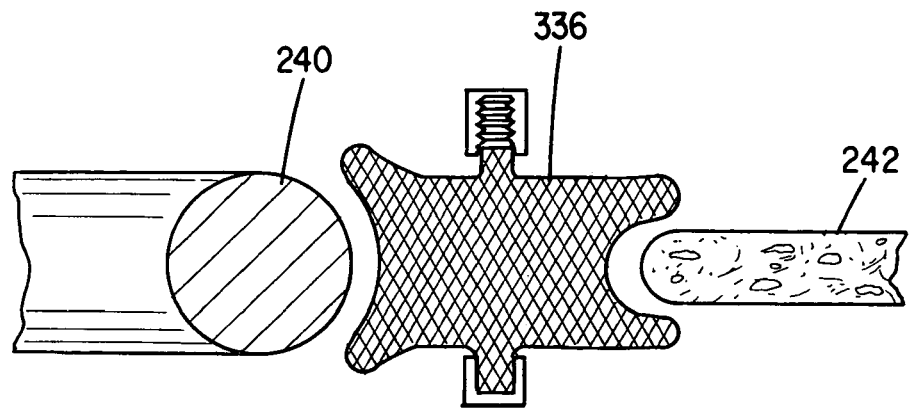

Since the PVL openings are of various shapes it is anticipated that a number of sizes and shapes of occluder devices may be needed to close these leaks. It is also important that the occluder be positioned securely to prevent migration or embolization of the device. As shown in FIG. 13b-I, device 300 is formed of two layers each having the same shape. FIG. 13b-II is a plan view of device 300 and FIG. 13b-III is an end view thereof. This particular design is intended to occlude openings that are somewhat oblong in shape. Radiopaque markers 330 may be placed either on the narrow or wide side of the expanded shape to help the physician orient the device as needed. These markers may be radiopaque platinum wire or platinum iridium markers attached to the braid in manner which does not impede braid collapse or self expansion. Since the wire diameter is small, the oblong shape can conform to shapes that may be more rounded or longer. FIG. 13c illustrates a crescent shaped occluder 324 and FIG. 13d illustrates a round occluder 326. In FIG. 13e, one edge of the device that interfaces with the cuff 240 is shaped to match the cuff shape whereas the other side that interfaces with the tissue 242 has a shape more conducive to the thickness of the tissue at the interface. For illustrative purposes, dimensions are given for the oblong occluder of FIG. 13b but are similar for other shapes where applicable. All dimensions are in mm.

A=6, B=2, C=10, D=6, E=6, F=9, G=7, H=2

Figure 13F:
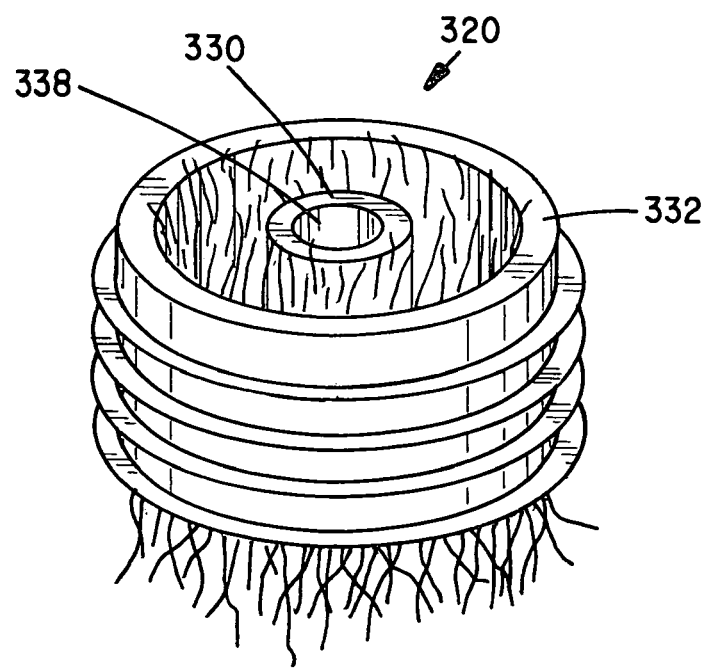

In FIG. 13f is shown a preferred clamp 320 for the device 300 intended to be compatible with delivery of the occluder over a guidewire. In this design the clamps 320 must have a central passage 328 for the guidewire to slidable pass there through. The clamp 320 is therefore fabricated with an inner ring 330 having an inside diameter slightly larger (about 0.002-0.004 inch) larger than the guidewire diameter. The clamp also has an outer ring 332 large enough to contain the braided wire ends between the two rings. The outer ring may be swaged to compress the outer ring against the wires and the inner ring or the wire ends and rings may be welded, brazed, soldered or held by adhesive or other known means. At least one of the clamps has threads either external on the outer ring of the clamp or internally in the inner ring. If internal threads are used the inner ring must be enlarged to accommodate a male threaded delivery device with an internal lumen sized for passage of a guide wire through the threaded clamp.

An over the guidewire delivery system is particularly useful in delivery of an occluder for PVL cases. One of the most difficult aspects of the case is delivering the device through the defect near the valve cuff Due to the turbulence of blood in the area of the valve it is preferable to place a small surface area steerable guidewire through the defect first and then advance the delivery device and catheter over the guidewire. Alternatively the guidewire may be placed through the catheter and delivery device and lead the passage of the system through the vasculature. Near the valve defect the guidewire may be independently maneuvered through the defect and then the catheter and delivery device may be advanced over the guidewire.

A method of treating a pera-valular leak may involve the following steps: (1) advance a guidewire through the vasculature of the body and across the pera-valular leak opening; (2) advance over the guidewire a catheter containing a occluder connected to a delivery device until the distal tip of the catheter crosses the pera valular leak opening; (3) deploy the distal portion (distal to waist) of the occluder by manipulating the deliver device to extend the distal portion of the occluder beyond the distal end of the catheter causing the distal portion to self expand toward it's preset shape; (4) pulling proximally the catheter and delivery device until the expanded portion of the occluder contacts tissue adjacent one side of the opening; (5) withdrawing the catheter proximally relative to the delivery device, to expose the remaining proximal portion of the occluder while allowing the deliver device to advance distally as the occluder self expands and contacts tissue adjacent the opposite side of the opening; (6) disconnecting the delivery device from the occluder once the device is placed properly to occlude the opening; and (7) removing the delivery device and catheter from the body.

An alternative method of treating a pera-valvular leak is similar to above but includes the step of: advancing the guidewire through the vasculature through a preshaped or steerable catheter to facilitate passage through the peri-valvular leak opening. An optional additional step includes: removing the catheter after crossing the leak opening and before delivery of the occluder.

Figure 14A:
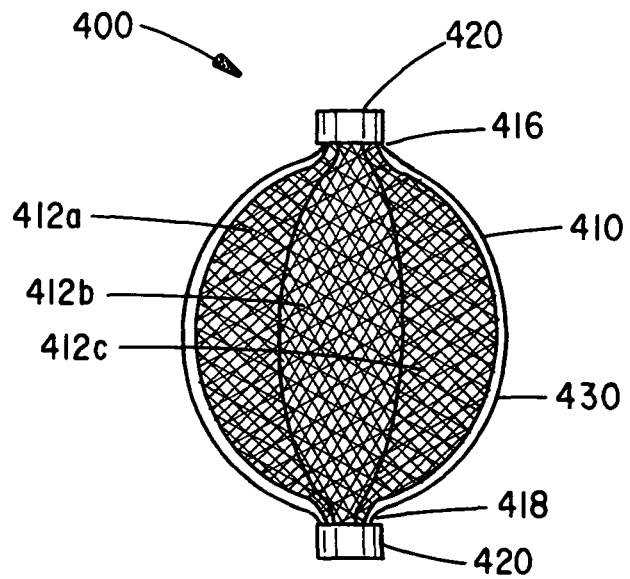
FIGS. 14a-14c are views of an embodiment having non coaxial inner braids.
Figure 14B:
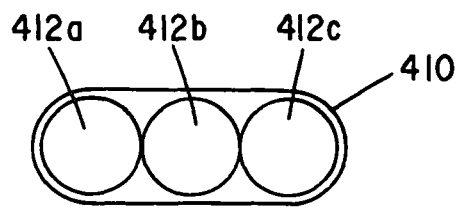
Figure 14C:
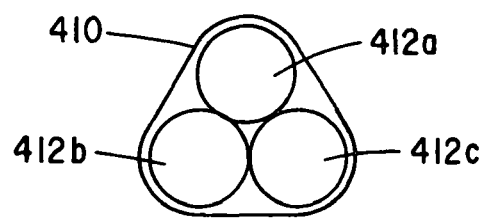

Another embodiment of an occluder is a variation of the devices shown in FIGS. 12a-12f, whereby the occluder device 400, as shown in FIGS. 14a-14c, consists of a soft, conformable, outer braid 410 enclosing a volume 430 that is pre-shaped as desired, with two or more internal braided tubular members 412a, b, c side by side with shared braid end wire connectors at least at one end. As can be seen in FIGS. 14b and 14c, the multiple braids need not be concentric. This arrangement allows the inner braided members 412 to shift relative to one another to fill the available volume of unknown size or shape such as an oblong, crescent, or oval cavity shape. This is accomplished by selecting a heat set shape for braids 412 that have a large enough diameter to exert force against the outer tubular braid to compel the outer braid against the wall of the cavity the device is placed in. To share a common end wire clamp the internal tubular braid walls must be compressed against each other at the ends and shaped into a crescent to fit in annular fashion about a wire end clamp as shown at clamp 420 of FIG. 14a. The proximal clamp 420 at wire end 418 contains threads (not shown) for connection to the delivery catheter, not shown. The proximal clamp 420 may or may not also clamp the ends of the inner braid proximal wire ends. It is preferable that the proximal wire ends of braids 412 be connected to clamp 420 by means of a tether or elastic member to allow for a braid length change that would vary based on the shape of the device 400 within a cavity. The outer braid for this embodiment could be a braid of 144 Nitinol wires of a diameter of between 0.001-0.002 inches. The inner braids may be fashioned from either 72 or 36. Nitinol wires with a diameter of 0.001-0.003 inches. An optional over the guidewire delivery embodiment is practical by using wire end clamps 420 that are of the two ring design as described in previous embodiments.

Figure 15:
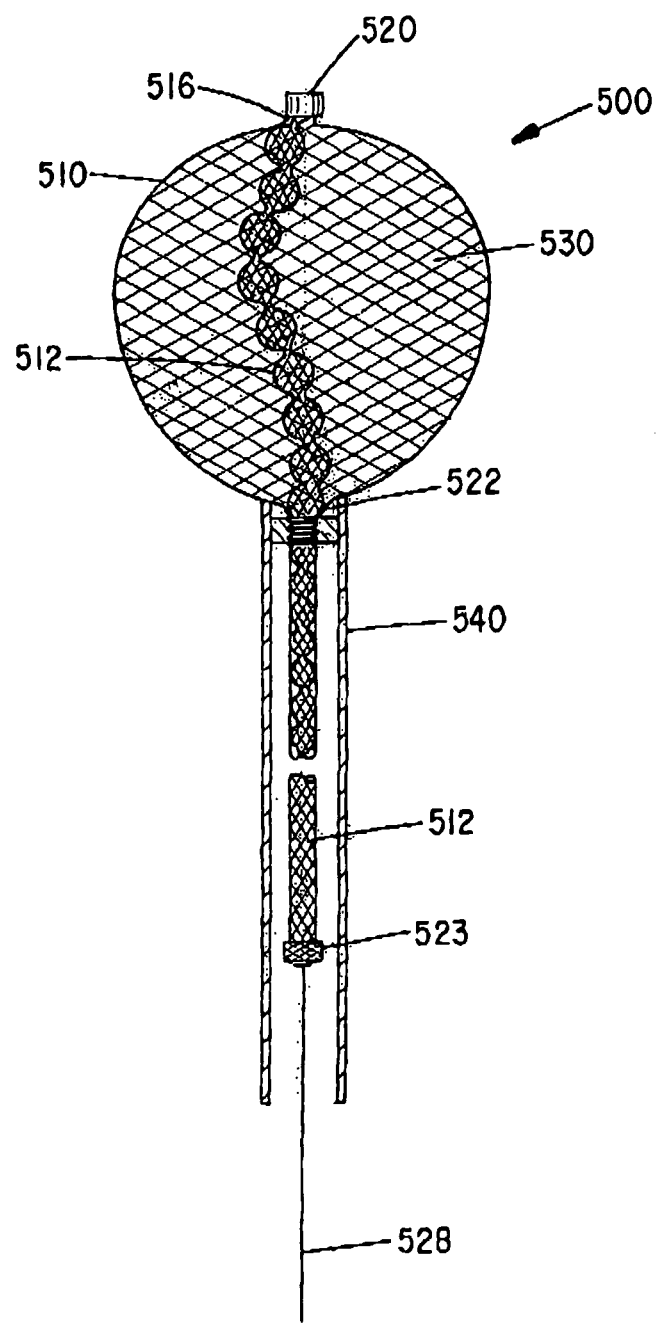
FIG. 15 is a drawing of an embodiment where by the inner braid fills the outer braid volume in serpentine fashion.

In a further embodiment 500 as shown in FIG. 15 the outer braid 510 is pre-shaped to define a particular volume shape 530. Contained within the outer braid and coaxially sharing the outer braid distal wire end clamp 520 is a smaller diameter tubular braid 512 that is pre-shaped into a bead and chain shape. The internal smaller braid 512 is much longer than the outer braid 510 and is designed to meander into the outer braid defined volume 530 as braid 512 is inserted to fill the volume completely and help the outer braid to conform to the cavity shape it is within. The distal braided wire end clamp 520 at wire end 516 is preferably a two part clamp arrangement with an internal ring and external ring pinching the braid wires between the rings. The proximal braided wire end clamp 522 is similarly constructed but the outer ring is threaded to mate with threads on the delivery catheter 540 for selective connection between the device and the delivery catheter. In this embodiment a portion of the inner braid remains within the delivery catheter when the outer braid is fully deployed. In order to deliver the balance of the inner tubular braid 512 into the volume 530, a pusher wire 528 within the delivery catheter 540 acts against the proximal end wire end clamp 523 of braid 512 to advance the braid completely out of the delivery catheter. The pusher wire 528 may optionally have a threaded end to engage with optional threads in the wire end clamp 523. The delivery catheter 540 would be advanced to the treatment site through a sheath. The high density of wire within the volume 530 aids in rapid hemostasis while maintaining a low profile for delivery. The spherical shape of the bead chain fills the volume with sphere against sphere against the outer braid and thereby loads the outer braid surface against the cavity wall desired to be occluded. For this embodiment, the outer braid should be soft and conformable. A braid of 144 Nitinol wires of 0.001-0.002 inch diameter should be suitable. The inner braid may be either 72 or 36 Nitinol wires and the wire diameter may be between 0.001 to 0.003 inch. The outer and inner braided layers are heat set as previously described in the desired volume shape and beaded chain shape as desired. The wire end clamps 520 and 523 may be of the two ring configuration as previously described in other embodiments to allow the device to be configured for over the guidewire delivery.

A method of occluding a body cavity consists of the following steps: (1) providing an occluder comprising at least a first self expanding braided tubular layer defining a preset volume shape and a second braided member longer than the first braided member in the collapsed for delivery configuration, the second braided member coaxially connected at one end to the end of the first braided layer, the second braided member having a repeating preset volume occupying shape much smaller than the preset shape of the first braided layer, whereby both first and second braided members have a collapsed elongated low profile shape for delivery through a catheter and a self expanding preset volume occupying space for occlusion of a body cavity; (2) advancing the distal tip of a delivery catheter containing the occluder and a delivery device to a body cavity; (3) advancing the distal end of the occluder out of the catheter to allow the occluder first braided layer to self expand within the cavity; advancing the second braided member distally within the volume occupied by the first braided layer until the entire self expanded second braided member is contained within the volume; (4) disconnecting the delivery device from the occluder; (5) removing the catheter and delivery device from the body. An optional additional step to the above method is to deliver the occluder, delivery device and catheter over a guidewire and removal of the guidewire from the cavity, prior to self expansion of the first braided layer.

Figure 16A:
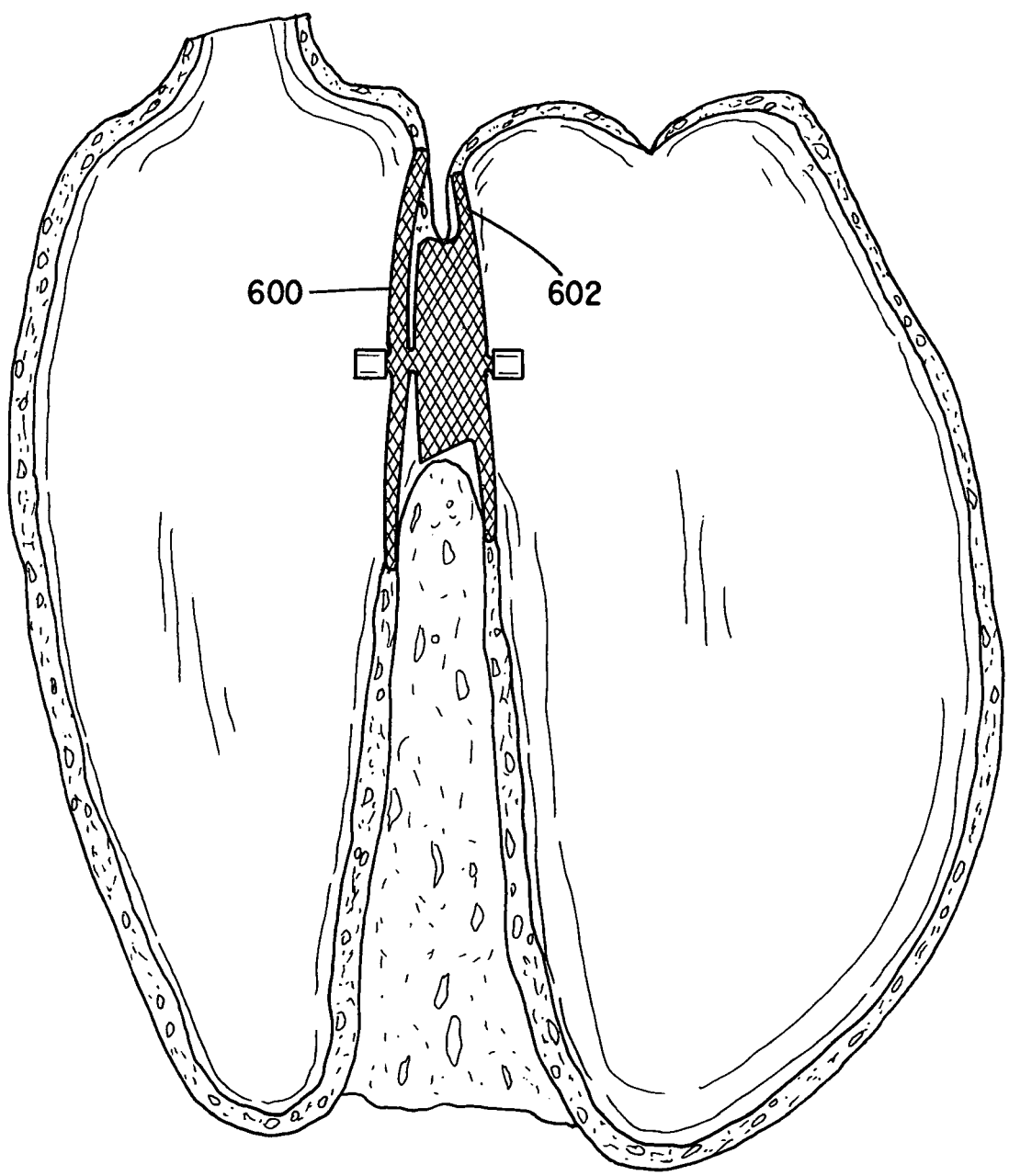
FIGS. 16a-16d are views of an alternative embodiment for treatment of para-membranous ventricular septal defects (PMVSD).
Figure 16B:
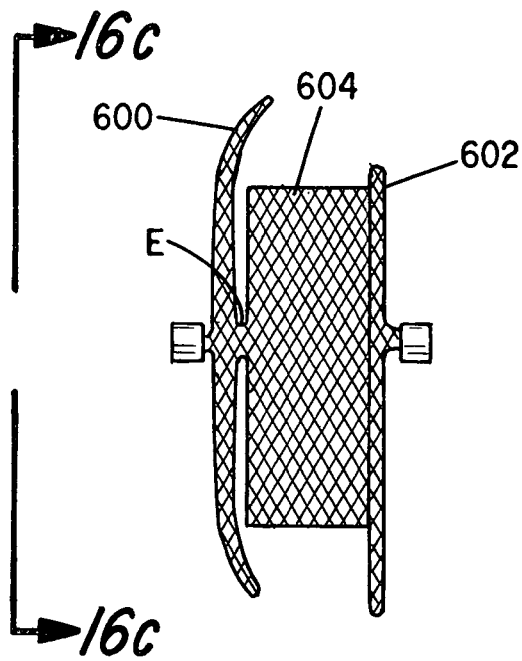
Figure 16D:
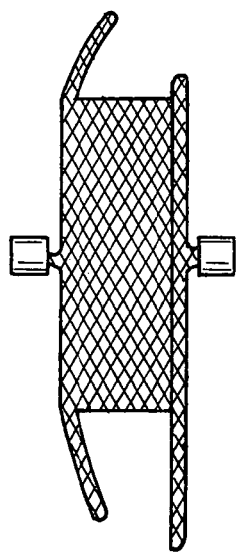
Figure 16C:
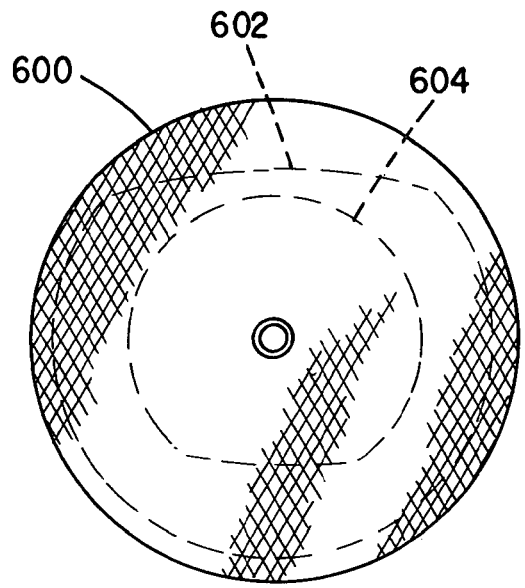

In another embodiment as shown in FIGS. 16a-16d, intended primarily for para-membranous VSD occlusion, the device central diameter is relieved with a flattened or inverted portion in the circumference to relieve pressure on the heart's conductive His bundle at the muscular portion of the septum, to prevent heart block (FIG. 16a). Additionally, the device has only one articulating flange 600 (right chamber) with a small diameter E and the flange 602 on the opposing end (left chamber) is relieved in diameter to prevent interference with the aortic valve. It is anticipated that the single articulating flange 600 will reduce pressure of the conductive His bundle to help prevent heart block and that the lack of articulation on the left chamber side will better resist dislodgement of the device from the higher arterial blood pressure (FIGS. 16b and 16c). An alternative embodiment for relieving the left chamber flange 602 diameter to prevent interference with the aortic valve is to move the left chamber flange off axis to the central device portion so the flange is displaced away from the valve as shown in FIG. 16d. Further modification, by eliminating both flange articulations is also anticipated as shown in FIG. 16d.

Although the dimensions given are for the PDA occlusion device, it is anticipated that this device shape or modifications to it could also be used for other occlusive applications such as for ASD, VSD, PFO, or any other similar abnormality. The central portion could alternatively be barrel shaped, spherical, or cylindrical in outer surface with straight or tapered end walls. The central portion may be bellows shaped to further accommodate passage length change, double cone shaped with a center point at the maximum diameter or any other shape as desired. Similarly the disks need not be tapered inward but this is preferred. The disks may be preformed in a non parallel manner and one disk may be of a size different from the other. Although this design is preferably 2 layers it is also anticipated that additional layers (3, 4, or more) may be used to fabricate the device. Also, the layers may be the same pick count and the same wire diameter or they may be varied in any order or manner as suited to a particular application. The preferred embodiment described, occludes relatively quickly compared to prior art devices due the small pore size and large surface area created by the multitude of wires in multiple layers, has a lower profile, improved retention force, and improved conformability to adjust to a variety of vessel passageways with minimal interference in the native vessel flow. The reduced profile of this device is sufficiently low to allow delivery through a 4 French catheter or sheath. The device 200 is also symmetrical so that is may be deliverable by catheter from either the pulmonary side or the aortic side as selected by the physician. The advantage of a venous approach for PDA closure is to potentially treat infants as small a 1 kg. The advantage of an arterial approach in slightly larger premature infants is that both angiography and device implant can take place from a common access point in the femoral artery.

Because of the significant increase in the number of wire strands in the composite multi-layer structure, it is no longer necessary to incorporate a sewn-in polyester material in order to reduce the time required to establish total occlusion of a PDA, VSD, ASD, PFO, PVL, or other vascular location. This not only reduces the cost of manufacture, but also facilitates loading of the resulting device into a delivery catheter of a reduced French size. Reduced French size means the ability to treat smaller vessels which is a major advantage. This invention also provides an occluder design that is more flexible, easy to track and more adaptive to variations in the geometry of the defect while providing improved clamping and less intrusion into the vasculature on either side of the defect. Over the guidewire tracking offer options for delivery to difficult to reach anatomy. Due to device symmetry, some embodiments are deliverable from either the venous or arterial side of the same defect.

This invention has been described herein in considerable detail in order to comply with the Patent Statutes and to provide those skilled in the art with the information needed to apply the novel principles and to construct and use embodiments of the example as required. However, it is to be understood that specifically different devices can carry out the invention and that various modifications can be accomplished without departing from the scope of the invention itself. For example, options shown for one embodiment could easily be applied to other embodiments. Although many embodiments are shown as being fabricated of two braided layers, more layers may be added to any embodiment, as desired for a particular application, without departing from the scope of this invention.

What is claimed is:

1. A collapsible medical device comprising an outer metal fabric layer surrounding an inner metal fabric layer, the outer and inner metal fabric layers each having a plurality of braided metal strands, the medical device including an expanded preset configuration with:

a central portion having a first and a second end and comprising an outer surface having tapered walls that taper outwardly from the first end to the second end, a first disk member at a first end of the medical device, the first disk member coaxial with the central portion and adjacent the first end of said central portion, wherein the first disk member is connected to the central portion at a reduced diameter portion that has a diameter less than a diameter of the central portion, and a second disk member at a second, opposing end of the medical device, the second disk member coaxial with the central portion and adjacent the second end of the central portion, each of said disk members being larger in diameter than the central portion, wherein the second disk member has an inner face continuous with the outer surface of the second end of the central portion, to create an occlusion of an abnormal opening in a location of a patient's vascular system, the expanded preset configuration being deformable to a lesser cross-sectional dimension for delivery through a channel in a patient's body, the outer and inner metal fabric layers having a memory property such that the medical device tends to return to said expanded preset configuration when unconstrained.

2. The medical device as in claim 1, wherein the number of braided metal strands comprising the outer metal fabric layer is 144.

3. The medical device as in claim 1, wherein the number of braided metal strands comprising the inner metal fabric layer is 144.

4. The medical device as in claim 1, wherein the diameter of the braided metal strands comprising the outer metal fabric layer is in a range from 0.001 to 0.003 inches.

5. The medical device as in claim 1, wherein the diameter of the braided metal strands comprising the inner metal fabric layer is in a range of from 0.001 to 0.003 inches.

6. The medical device as in claim 1, wherein the braided metal strands comprising the outer metal fabric layer are comprised of shape memory Nitinol wire.

7. The medical device as in claim 1, wherein the braided metal strands comprising the inner metal fabric layer are comprised of shape memory Nitinol wire.

8. The medical device as in claim 1, wherein the medical device is sized for delivery through a 4-7 French catheter when deformed to the lesser cross-sectional dimension.

9. The medical device as in claim 1, wherein one of the first and said second disk members comprises an inner diameter portion perpendicular to a longitudinal axis of the central portion and a disk outer diameter portion circumferentially surrounding the inner diameter portion, wherein the disk outer diameter portion is angled toward the central portion.

10. The medical device as in claim 9, wherein the other of the first and the second disk members is planar and perpendicular to the longitudinal axis of the central portion.

11. The medical device as in claim 1, further comprising a clamp coupling together proximal ends of the inner and outer metal fabric layers, the clamp defining a bore for receiving a distal end of a delivery device.

12. The medical device as in claim 1, wherein the central portion has a proximal diameter at the first end and a distal diameter at the second end, wherein the proximal diameter is less than the distal diameter.

13. The medical device as in claim 12, wherein the diameter of the first and second disk members is greater than the distal diameter of the central portion.

14. The medical device as in claim 1, wherein the first disk member has an inner face that is concave towards the central portion.

* * * * *